(12) United States Patent
Zhang et al.

(10) Patent No.: US 8,524,467 B2
(45) Date of Patent: Sep. 3, 2013

(54) DIAGNOSTIC AND THERAPEUTIC TARGETS FOR LEUKEMIA

(75) Inventors: Yi Zhang, Chapel Hill, NC (US); Yuki Okada, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1244 days.

(21) Appl. No.: 12/161,482

(22) PCT Filed: Dec. 6, 2006

(86) PCT No.: PCT/US2006/046612
§ 371 (c)(1),
(2), (4) Date: Nov. 14, 2008

(87) PCT Pub. No.: WO2007/087015
PCT Pub. Date: Aug. 2, 2007

(65) Prior Publication Data
US 2009/0061443 A1    Mar. 5, 2009

Related U.S. Application Data

(60) Provisional application No. 60/760,709, filed on Jan. 20, 2006.

(51) Int. Cl.
*C12Q 1/68* (2006.01)
*G01N 33/00* (2006.01)
*G01N 33/53* (2006.01)
*G01N 33/542* (2006.01)
*G01N 33/567* (2006.01)
*G01N 33/574* (2006.01)

(52) U.S. Cl.
USPC .............. 435/7.9; 435/4; 435/7.21; 435/7.23; 435/7.24; 435/7.6; 435/7.72

(58) Field of Classification Search
None
See application file for complete search history.

(56) References Cited

U.S. PATENT DOCUMENTS

| | | | |
|---|---|---|---|
| 6,251,594 B1 | 6/2001 | Gonzalgo et al. | |
| 6,555,329 B2 | 4/2003 | Jenuwein et al. | |
| 7,442,685 B2 | 10/2008 | Zhang et al. | |
| 2003/0157532 A1 | 8/2003 | Jenuwein et al. | |
| 2004/0053233 A1 | 3/2004 | Lorens et al. | |
| 2005/0048634 A1 | 3/2005 | Zhang et al. | |

FOREIGN PATENT DOCUMENTS

| | | |
|---|---|---|
| WO | WO 03/016497 A2 | 2/2003 |
| WO | WO 2006/025832 A1 | 3/2006 |

OTHER PUBLICATIONS

Chamberlain et al. Innovations and strategies for the development of anticancer vaccines. Expert Opinion on Pharmacotherapy. 1(4): 603-614, 2000.*
Gura. Systems for identifying new drugs are often faulty. Science 278: 1041 and 1042, Nov. 7, 1997.*
Bodey et al. Failure of cancer vaccines: the significant limitations of this approach to immunotherapy. Anticancer Research 20: 2665-2676, 2000.*
Segeren et al., "The FAB classification for acute myeloid leukaemia—is it outdated?" The Netherlands Journal of Medicine 49:126-131 (1996).
Supplementary European Search Report, European Application No. EP 06839119, dated Dec. 30, 2009 (12 pages).
Ayton et al., "Molecular mechanisms of leukemogenesis mediated by MLL fusion proteins", Oncogene, vol. 20, pp. 5695-5707 (2001).
Ayton et al., "Transformation of myeloid progenitors by MLL oncoproteins is dependent on Hoxa7 and Hoxa9", Genes & Development, vol. 17, pp. 2298-2307 (2003).
Beverloo et al., "Breakpoint Heterogeneity in t(10;11) Translocation in AML-M4/M5 Resulting in Fusion of *AF10* and *MLL* Is Resolved by Fluorescent in Situ Hybridization Analysis'", Cancer Research, vol. 55, pp. 4220-4224 (Oct. 1, 1995).
Bracken et al., "EZH2 is downstream of the pRB-E2F pathway, essential for proliferation and amplified in cancer", The EMBO Journal, vol. 22:20, pp. 5323-5335 (2003).
Carlson et al., "Identification and molecular characterization of CALM/AF10 fusion products in T cell acute lymphoblastic leukemia and acute myeloid leukemia", Leukemia, vol. 14, pp. 100-104 (2000).
Crooks et al., "Constitutive *HOXA5* Expression Inhibits Erythropoiesis and Increases Myelopoiesis From Human Hematopoietic Progenitors", Blood Journal, vol. 94, pp. 519-528 (1999).
Dik et al., "CALM-AF10+ T-ALL expression profiles are characterized by overexpression of *HOXA* and *BMI1* oncogenes", Leukemia, vol. 19, pp. 1948-1957 (2005).
DiMartino et al., "The AF10 leucine zipper is required for leukemic transformation of myeloid progenitors by MLL-AF10", Blood Journal, vol. 99, pp. 3780-3785 (2002).
Dlakić, M.; "Chromatin silencing protein and pachytene checkpoint regulator Dot1 p has a methyltransferase fold," *TRENDS in Biochemical Sciences* 26:7, 405-407 (Jul. 2001).
Drabkin et al., "Quantitative HOX expression in chromosomally defined subsets of acute myelogenous leukemia", Leukemia, vol. 16, pp. 186-195 (2002).
Dreyling et al., "*MLL* and *CALM* are Fused to *AF10* in Morphologically Distinct Subsets of Acute Leukemia With Translocation t(10;11): Both Rearrangements Are Associated With a Poor Prognosis", Blood Journal, vol. 91:12, pp. 4662-4667 (Jun. 15, 1998).
Dreyling et al., "The t(10;11)(p13;q14)in the U937 cell line results in the fusion of the AF10 gene and *CALM*, encoding a new member of the AP-3 clathrin assembly protein family", Proc. Natl. Acad. Sci. USA, vol. 93, pp. 4804-4809 (May 1996).

(Continued)

*Primary Examiner* — Alana Harris Dent
(74) *Attorney, Agent, or Firm* — Sterne, Kessler, Goldstein & Fox P.L.L.C.

(57) ABSTRACT

The present invention relates to methods of identifying candidate compounds for the treatment of leukemia and diagnostic methods based on histone methylation and HoxA5 promoter activity.

13 Claims, 15 Drawing Sheets

(56) References Cited

OTHER PUBLICATIONS

Feng et al.; "Methylation of H3-Lysine 79 is mediated by a new family of HMTases without a SET domain," *Current Biology* 12: 1052-1058 (Jun. 2002).

Kleer et al., "EZH2 is a marker of aggressive breast cancer and promotes neoplastic transformation of breast epithelial cells", PNAS, vol. 100:20, pp. 11606-11611 (Sep. 30, 2003).

Kobayashi et al., "Hematologic Malignancies With the t(10;11)(p13;q21) Have the Same Molecular Event and a Variety of Morphologic or Immunologic Phenotypes", Genes, Chromosomes & Cancer, vol. 20, pp. 253-259 (1997).

Kobayashi et al., "U937 Cell line Has a t(10;11)(p13-14;q14-21) Rather Than a Deletion of 11q", Genes, Chromosomes & Cancer, vol. 13, pp. 217-218 (1995).

Lacoste et al., "Disruptor of Telomeric Silencing-1 is a chromosome-specific histone H3 methyltransferase," *Journal of Biological Chemistry* 277:34 30421-30424 (2002).

Meyerholz et al., "Effect of Clathrin Assembly Lymphoid Myeloid Leukemia Protein Depletion on Clathrin Coat Formation", Traffic, vol. 6, pp. 1225-1234 (2005).

Milne et al., "MLL Targets Set Domain Methyltransferase Activity to *Hox* Gene Promoters", Molecular Cell, vol. 10, pp. 1107-1117 (Nov. 2002).

Min et al., "Structure of the catalytic domain of human DOT1L, a non-set domain nucleosomal histone methyltransferase," *Cell* 112: 711-723 (Mar. 2003).

Nakamura et al., "ALL-1 Is a Histone Methyltransferase that Assembles a Supercomplex of Proteins Involved in Transcriptional Regulation", Molecular Cell, vol. 10, pp. 1119-1128 (Nov. 2002).

Ng et al., "Lysine methylation within the globular domain of histone H3 by Dot1 is important for telomeric silencing and Sir protein association," *Genes & Development* 16: 1518-1527 (2002).

Okada et al., "hDOT1L Links Histone Methylation to Leukemogenesis", Cell, vol. 121, pp. 167-178 (Apr. 22, 2005).

Okada et al., "Leukaemic transformation by CALM-AF10 involves upregulation of Hoxa5 by hDOT1L", Nature Cell Biology, vol. 8:9, pp. 1017-1024 (Sep. 2006).

Quentmeier et al., "Expression of *HOX* Genes in Acute Leukemia Cell Lines with and without *MLL* Translocations", Leukemia & Lymphoma, vol. 45, pp. 567-574 (Mar. 2004).

San-Segundo et al., "Role for the silencing protein Dot1 in Meiotic checkpoint control," *Molecular Biology of the Cell* 11 3601-3615 (Oct. 2000).

Schneider et al., "Unsafe SETs: histone lysine methyltransferases and cancer", Trends in Biochemical Sciences, vol. 27:8, pp. 396-402 (Aug. 2002).

Singer et al., "Identification of high-copy disruptors of telomeric silencing in *Saccharomyces cerevisiae,*" *Genetics* 150 613-632 (Oct. 1998).

So et al., "Leukemic transformation of hematopoietic progenitors by MLL-GAS7 in the absence of *Hoxa7* or *Hoxa9*", Blood Journal, vol. 103:8, pp. 3192-3199 (Apr. 15, 2004).

Soulier et al., "HOXA genes are included in genetic and biologic networks defining human acute T-cell leukemia (T-ALL)", Blood Journal, vol. 106, pp. 274-286 (2005).

Tebar et al., "Clathrin Assembly Lymphoid Myeloid Leukemia (CALM) Protein: Localization in Endocytic-coated Pits, Interactions with Clathrin, and the Impact of Overexpression on Clathrin-mediated Traffic", Molecular Biology of the Cell, vol. 10, pp. 2687-2702 (Aug. 1999).

Van Leeuwen, et al., "Dot1p modulates silencing in yeast by methylation of the nucleosome core", *Cell* 109 745-756 (Jun. 2002).

Varambally et al., "The polycomb group protein EZH2 is involved in progression of prostate cancer", Nature, vol. 419, pp. 624-629 (Oct. 10, 2002).

Vecchi et al., "Nucleocytoplasmic Shuttling of Endocytic Proteins", The Journal of Cell Biology, vol. 153:7, pp. 1511-1517 (Jun. 25, 2001).

Zeisig et al., "*Hoxa9* and *Meis1* Are Key Targets for MLL-ENL-Mediated Cellular Immortalization", Molecular and Cellular Biology, vol. 24, pp. 617-628 (Jan. 2004).

Zhang et al. (Oral and Poster Presentations) "Role of histone methylation and ubiquitination in PcG silencing," Cold Spring Harbor 69th Symposium: Epigenetics, Cold Spring Harbor, NY, USA (Jun. 2-7, 2004).

Zhang, Yi, (Oral Presentation) "hDOT1L, a histone methyltransferase without a SET domain is involved in leukemogenesis," 28th Lineberger Cancer Symposium, "Epigenetics, Chromatin and Cancer," UNC-CH, Chapel Hill, NC, USA (Apr. 20, 2004).

\* cited by examiner

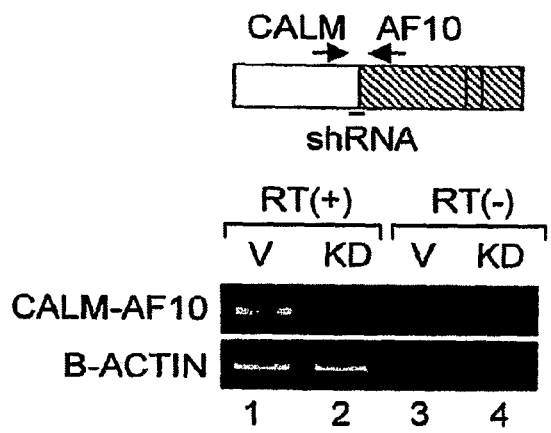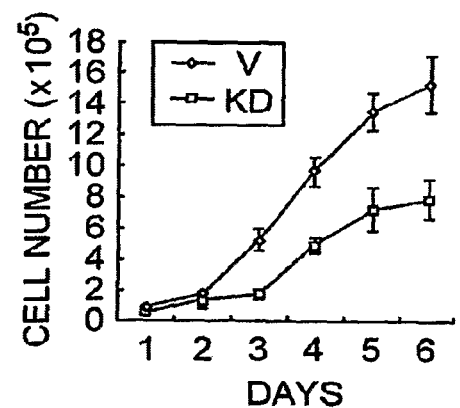
FIG. 1A  FIG. 1B
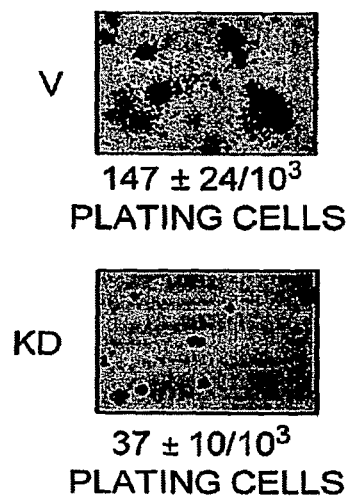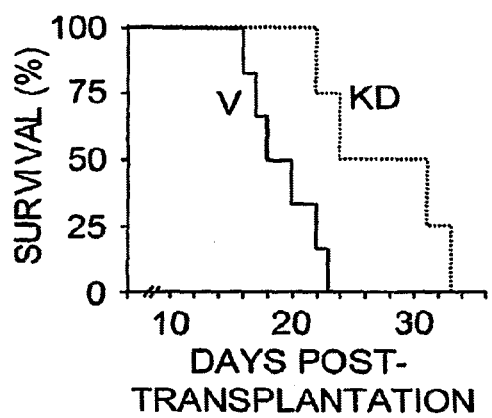
FIG. 1C  FIG. 1D

DIAGNOSTIC AND THERAPEUTIC TARGETS FOR LEUKEMIA

RELATED APPLICATION INFORMATION

This application claims the benefit under 35 U.S.C. §371 from PCT Application No. PCT/US2006/046612, filed 6 Dec. 2006, the disclosure of which is incorporated by reference herein in its entirety, which claims the benefit of U.S. Provisional Application Ser. No. 60/760,709, filed 20 Jan. 2006, the disclosure of which is incorporated by reference herein in its entirety.

STATEMENT OF FEDERAL SUPPORT

This invention was made with federal support under Grant No. GM68804 awarded by the National Institutes of Health. The United States government has certain rights in the invention.

FIELD OF THE INVENTION

The present invention relates to methods of identifying candidate compounds for the treatment of leukemia and diagnostic methods based on histone methylation.

BACKGROUND OF THE INVENTION

Higher-order chromatin structures are of profound importance in gene regulation and epigenetic inheritance (Wu and Grunstein (2000) *Trends Biochem. Sci.* 25:619-623). Post-translational modifications of core histones influence the establishment and maintenance of higher-order chromatin structures. The unstructured tails of certain core histones are extensively modified by acetylation, methylation, phosphorylation, ribosylation and ubiquitination. A "histone code" hypothesis, linking histone modifications to chromatin structures, has been the focus of intensive recent studies (Strahl and Allis (2000) *Mol. Cell. Biol.* 22:1298-1306; Turner (2000) *Bioessays* 22:836-845). Histone methylation has emerged as a major form of histone modification. (Strahl and Allis (2000) *Mol. Cell. Biol.* 22:1298-1306; Zhang and Reinberg (2001) *Genes Dev.* 15:2343-2360). In particular, a large family of SET domain-containing histone methyltransferases (HMTases) has been identified (Lachner and Jenuwein (2002) *Curr. Opin. Cell Biol.* 14:286-298). SET domain proteins have been shown to methylate various N-terminal lysine residues of histone H3 and H4. Histone lysine methylation has been associated with diverse biological processes ranging from transcriptional regulation to the faithful transmission of chromosomes during cell division (Grewal and Elgin (2002) *Curr. Opin. Genet. Dev.* 12:178-187).

Further, lysine methylation catalyzed by SET domain containing proteins has been linked to cancer (Schneider, et al. (2002) *Trends Biochem. Sci.* 27:396-402). For example, the H3-K4 methyltransferase MLL is frequently translocated in leukemia (Ayton and Cleary (2001) *Oncogene* 20:5695-5707; Milne, et al. (2002) *Mol. Cell* 10:1107-1117; Nakamura, et al. (2002) *Mol. Cell* 10:1119-1128) and the H3-K27 methyltransferase EZH2 is overexpressed in a number of tumors and its expression level correlates with the invasiveness of these tumors (Bracken, et al. (2003) *EMBO J.* 22:5323-5335; Kleer, et al. (2003) *Proc. Natl. Acad. Sci. USA* 100:11606-11611; Varambally, et al. (2002) *Nature* 419:624-9).

Dot1 is an evolutionarily conserved protein that was originally identified in *S. cerevisiae* as a disrupter of telomeric silencing (Singer, et al. (1998) *Genetics* 150:613-632). It also functions at the pachytene checkpoint during the meiotic cell cycle (San-Segundo and Roeder (2000) *Mol. Biol. Cell.* 11:3601-3615). Sequence analysis of yeast Dot1 revealed that it possesses certain characteristic SAM binding motifs, similar to the ones in protein arginine methyltransferases (Dlakic (2001) *Trends Biochem. Sci.* 26:405-407).

It has recently been demonstrated that hDOT1L is a histone H3-K79 methyltransferase (Feng et al., (2002) *Curr. Biol.* 12:1052-1058), and plays an important role in MLL-AF10-mediated leukemogenesis (Okada et al., (2005) *Cell* 121:167-78). It was shown that mistargeting of hDOT1L to the Hoxa9 gene by MLL-AF10 results in H3-K79 methylation and Hoxa9 upregulation which contributes to leukemic transformation (Okada et al., (2005) *Cell* 121:167-78). It was further demonstrated that the hDOT1L and MLL-AF10 interaction involves the OM-LZ (octapeptide motif-leucine zipper) region of AF10, required for MLL-AF10-mediated leukemic transformation (DiMartino et al., (2002) *Blood* 99:3780-5).

SUMMARY OF THE INVENTION

The inventors demonstrate herein for the first time that: (1) CALM-AF10 fusion appears to be both necessary and sufficient to mediate leukemogenesis in vitro and in vivo; (2) that hDOT1L and its H3-K79 methyltransferase activity are implicated in CALM-AF10 mediated leukemic transformation; and (3) that the Hoxa5 gene is involved in CALM-AF10 mediated transformation. While not wishing to be limited by any theory of the invention, the inventors also provide an experimental model where hDOT1L retains nuclear localization of CALM-AF10 through protein-protein interaction. CALM-AF10 in association with hDOT1L is then recruited to the Hoxa5 promoter to mediate H3-K79 methylation which in turn leads to Hoxa5 upregulation and leukemogenesis.

Chromosomal translocation is one of the major causes of human cancer, particularly in acute leukemias. A translocation of t(10;11)(p12-13;q14-q23), which generates the chimeric gene CALM-AF10, is observed in various types of leukemias including T-ALL (T cell acute lymphoid leukemia) and AML (acute myeloid leukemia) (Carlson et al., (2000) *Leukemia* 14:100-104; Dreylng et al., (1998) *Blood* 91:4662-7). Although this chromosomal translocation is sometimes difficult to distinguish from a translocation of t(10;11)(p13;q23), which generates the chimeric gene MLL-AF10, patients with MLL-AF10 develop AML exclusively (Beverloo et al et al., (1995) *Cancer Res.* 55:4220-4). There are also noticeable differences in the AML mediated by CALM-AF10 and MLL-AF10. For example, the AML mediated by CALM-AF10 belongs to the M0/1 subtype, while the AML mediated by MLL-AF10 belongs to the M4/5 subtype (Dreylng et al., (1998) *Blood* 91:4662-7; Beverloo et al et al., (1995) *Cancer Res.* 55:4220-4). Although the role of MLL (mixed lineage leukemia) in hematopoiesis and leukemogenesis has been established, the underlying molecular mechanism is just beginning to be elucidated (Ayton et al., (2001) *Oncogene* 20:5695-5707; Daser et al., (2004) *Genes Dev.* 18:965-74; Hess, (2004) *Crit. Rev. Eukaryot. Gene Expr.* 14:235-54). Unlike MLL, the function of CALM (clathrin assembly lymphoid myeloid leukemia) in hematopoiesis and leukemia is completely unknown because CALM protein is located in the cytoplasm without the translocation, where it plays a role in clathrin-mediated trafficking (Dreyling et al., (1996) *Proc Natl Acad Sci* 93:4804-9; Tebar et al., (1999) *Mol Biol. Cell* 10:2687-702). In fact, the leukemic transformation capability of CALM-AF10 has not been experimentally demonstrated.

Accordingly, as a first aspect, the present invention provides a method of identifying a candidate compound for the prevention and/or treatment of leukemia, the method comprising:

contacting a DOT1L polypeptide with a CALM-AF10 fusion protein in the presence of a test compound under conditions sufficient for binding of the DOT1L polypeptide to the CALM-AF10 fusion protein; and detecting interaction between the DOT1L polypeptide and the CALM-AF10 fusion protein, wherein a reduction in interaction between the DOT1L polypeptide and the CALM-AF10 fusion protein in the presence of the test compound as compared with the level of interaction in the absence of the test compound indicates that the test compound is a candidate compound for the prevention and/or treatment of leukemia.

The invention further provides a method of identifying a candidate compound for the prevention and/or treatment of leukemia, the method comprising:

contacting a CALM-AF10 fusion protein with a test compound under conditions sufficient for binding of the test compound to the CALM-AF10 fusion protein; and detecting binding between the test compound and the CALM-AF10 fusion protein, wherein binding of the test compound to the CALM-AF10 fusion protein indicates that the test compound is a candidate compound for the prevention and/or treatment of leukemia.

As a further aspect, the invention provides a method of identifying a candidate compound for the prevention and/or treatment of leukemia, the method comprising:

contacting a nucleic acid comprising a HoxA5 promoter region with a CALM polypeptide or CALM-AF10 fusion protein in the presence of a test compound under conditions sufficient for binding of the CALM polypeptide or CALM-AF10 fusion protein to the HoxA5 promoter; and detecting interaction of the CALM polypeptide or CALM-AF10 fusion protein with the HoxA5 promoter, wherein a reduction in interaction between the CALM polypeptide or CALM-AF10 fusion protein with the HoxA5 promoter in the presence of the test compound as compared with the level of interaction in the absence of the test compound indicates that the test compound is a candidate compound for the prevention and/or treatment of leukemia.

As still another aspect, the invention provides a method of identifying a candidate compound for the prevention and/or treatment of leukemia, the method comprising:

contacting a nucleic acid comprising a HoxA5 promoter region with a DOT1L polypeptide and a CALM-AF10 fusion protein in the presence of a test compound under conditions sufficient for binding of the DOT1L polypeptide and the CALM-AF10 fusion protein to form a complex and for the complex to bind to the HoxA5 promoter; and detecting interaction of the DOT1L/CALM-AF10 complex to the HoxA5 promoter, wherein a reduction in interaction of the DOT1L/CALM-AF10 complex with the HoxA5 promoter in the presence of the test compound as compared with the level of interaction in the absence of the test compound indicates that the test compound is a candidate compound for the prevention and/or treatment of leukemia.

As yet a further aspect, the invention provides a method of identifying a candidate compound for the prevention and/or treatment of leukemia, the method comprising:

contacting a nucleic acid comprising a HoxA5 promoter region and/or any other portion of the HoxA5 gene with a test compound under conditions sufficient for the test compound to bind to the HoxA5 promoter region and/or the any other portion of the HoxA5 gene; and detecting binding between the test compound and the HoxA5 promoter and/or the any other portion of the HoxA5 gene, wherein binding between the test compound and the HoxA5 promoter and/or the any other portion of the HoxA5 gene indicates that the test compound is a candidate compound for the prevention and/or treatment of leukemia.

As another aspect, the invention provides a method of identifying a candidate compound for the prevention and/or treatment of leukemia, the method comprising:

contacting a nucleic acid comprising a HoxA5 promoter region with a test compound under conditions sufficient for HoxA5 promoter activity; and detecting HoxA5 promoter activity, wherein a reduction in HoxA5 promoter activity in the presence of the test compound as compared with the level of HoxA5 promoter activity in the absence of the test compound indicates that the test compound is a candidate compound for the prevention and/or treatment of leukemia.

In other embodiments, the invention provides a method of identifying a candidate compound for the prevention and/or treatment of T cell acute lymphoid leukemia (T-ALL) or acute myeloid leukemia subtype M0/1 (AML-M0/1):

contacting a DOT1L polypeptide with a histone or nucleosome substrate comprising histone H3 in the presence of a test compound;

detecting histone H3 lysine 79 (H3-K79) methylation of the substrate under conditions sufficient to provide H3-K79 methylation;

wherein an reduction in H3-K79 methylation in the presence of the test compound as compared with the level of H3-K79 methylation in the absence of the test compound indicates that the test compound is a candidate compound for the prevention and/or treatment of T-ALL or AML subtypes M0/1.

As another aspect, the invention provides a method of identifying a candidate compound for the prevention and/or treatment of T-ALL or AML-M0/1:

contacting a DOT1L polypeptide with AF10 under conditions sufficient for binding of the DO1L polypeptide to AF10;

detecting interaction between the DOT1L polypeptide and AF10;

wherein a reduction in interaction between DOT1L polypeptide and AF10 in the presence of the test compound as compared with the level of binding in the absence of the test compound indicates that the test compound is a candidate compound for the prevention and/or treatment of T-ALL or AML subtypes M0/1.

The invention also encompasses diagnostic methods. As one aspect, the invention provides a method of diagnosing whether a subject has or is at risk for developing leukemia and/or determining the prognosis for the course of the disease, the method comprising:

obtaining a biological sample comprising histones (e.g., nucleosomes) from a subject;

detecting histone H3 lysine 79 (H3-K79) methylation associated with the HoxA5 gene;

wherein an increase in HoxA5-associated H3-K79 methylation in the biological sample as compared with the level of HoxA5-associated H3-K79 methylation in a non-leukemic biological sample is diagnostic that the subject has or is at risk of developing leukemia and/or is prognostic of the course of the disease in the subject.

As still another aspect, the invention provides a method of diagnosing whether a subject has or is at risk for developing leukemia and/or determining the prognosis for the course of the disease, the method comprising determining HoxA5 promoter activity in the subject.

These and other aspects of the invention are set forth in more detail in the description of the invention below.

BRIEF DESCRIPTION OF THE DRAWINGS

FIGS. 1A-F. Knockdown of CALM-AF10 in U937 cells impairs their proliferation and leukemogenesis in vitro and in vivo. a, Top panel depicts the fusion protein and the target region for knockdown. The two arrows indicate the primer position used for RT-PCR. Bottom panel is RT-PCR results evaluating the knockdown efficiency. β-actin serves as a control. V: vector control, KD: Knockdown. b, c, Effects of CALM-AF10 knockdown on cell proliferation in RPMI medium (b) and methylcellulose (c). Only colonies having over 50 cells were counted. The numbers below the pictures in c represent colony numbers with standard deviation. d-f, Effects of CALM-AF10 knockdown in vivo. d, Knockdown CALM-AF10 extends survival time of transplanted mice when compared with those receiving transplantation of parental U937 cells. e, H&E staining demonstrating that mice transplanted with CALM-AF10 knockdown cells (bottom panels) have less infiltration of leukemic cells in spleen, kidney and pancreas when compared with mice transplanted with control U937 cells (top panels). Arrows indicate infiltration of transplanted U937 cells. Original magnification: ×40 for spleen, ×20 for others. f, FACS analysis of proliferation in bone marrow and spleen of transplanted U937 hCD45 positive cells. CALM-AF10 knockdown affects U937 cell proliferation in both bone marrow and spleen.

DETAILED DESCRIPTION OF THE INVENTION

Figure 1E:
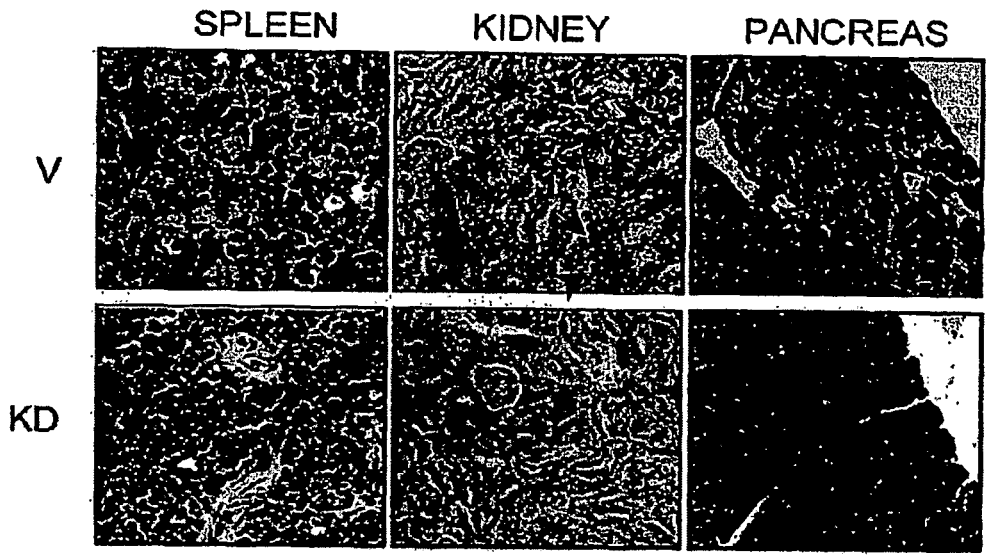

Chromatin structure is important in gene regulation and epigenetic inherence. It is known that post-translational modifications of histones are involved in the establishment and maintenance of higher-order chromatin structure; further, it has been reported that the tails of certain core histones are modified by acetylation, methylation, phosphorylation, ribosylation and ubiquitination. The present invention is based, in part, on the first demonstration that (1) CALM-AF10 fusion appears to be both necessary and sufficient to mediate leukemogenesis in vitro and in vivo; (2) that hDOT1L and its H3-K79 methyltransferase activity are implicated in CALM-AF10 mediated leukemic transformation; and (3) that the Hoxa5 gene is involved in CALM-AF10 mediated transformation. While not wishing to be limited to any theory of the invention, the inventors also provide an experimental model where hDOT1L retains nuclear localization of CALM-AF10 through protein-protein interaction. CALM-AF10 in association with hDOT1L is then recruited to the Hoxa5 promoter to mediate H3-K79 methylation, which in turn leads to Hoxa5 upregulation and leukemogenesis.

The present invention will now be described with reference to the accompanying drawings, in which preferred embodiments of the invention are shown. This invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

As used herein, the term "polypeptide" includes both proteins and peptides.

In particular embodiments, the polypeptides used in the practice of the present invention are "isolated" polypeptides. An "isolated" polypeptide as used herein is a polypeptide that is separated or substantially free from at least some of the other components of the naturally occurring organism or virus, for example, the cell or viral structural components or other polypeptides or nucleic acids commonly found associated with the polypeptide. In particular embodiments, the "isolated" polypeptide is at least about 1%, 5%, 10%, 25%, 50%, 60%, 70%, 75%, 80%, 85%, 90%, 95%, 97%, 98%, 99% or more pure (w/w). In other embodiments, an "isolated" polypeptide indicates that at least about a 5-fold, 10-fold, 25-fold, 100-fold, 1000-fold, 10,000-fold, or more enrichment of the protein (w/w) is achieved as compared with the starting material.

In particular embodiments, the nucleic acids used in the present invention are "isolated" nucleic acids. As used herein, an "isolated" nucleic acid means a nucleic acid separated or substantially free from at least some of the other components of the naturally occurring organism, such as for example, the cell structural components or other polypeptides or nucleic acids commonly found associated with the nucleic acid. In particular embodiments, the "isolated" nucleic acid is at least about 1%, 5%, 10%, 25%, 50%, 60%, 70%, 75%, 80%, 85%, 90%, 95%, 97%, 98%, 99% or more pure (w/w). In other embodiments, an "isolated" nucleic acid indicates that at least about a 5-fold, 10-fold, 25-fold, 100-fold, 000-fold, 10,000-fold, 100,000-fold or more enrichment of the nucleic acid (w/w) is achieved as compared with the starting material.

As used herein, the term "expression" (and grammatical equivalents) with reference to a nucleic acid refers to transcription of the nucleic acid and, optionally translation.

The term "modulate" (and grammatical equivalents) refers to an increase or decrease. In particular embodiments, the term "increase" or "enhance" (and grammatical equivalents) means an elevation by at least about 25%, 50%, 75%, 2-fold, 3-fold, 5-fold, 10-fold, 15-fold, 20-fold or more. In particular embodiments, the terms "decrease" or "reduce" (and grammatical equivalents) means a diminishment by at least about 25%, 40%, 50%, 60%, 75%, 80%, 85%, 90%, 95%, 98% or more. In some embodiments, the indicated activity, substance or other parameter is not detectable.

By the term "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The term "treat," "treats," "treating," or "treatment of" and the like also include prophylactic treatment of the subject (e.g., to prevent the onset of infection or cancer). As used herein, the term "prevent," "prevents," or "prevention" (and grammatical equivalents thereof) are not meant to imply complete abolition of disease and encompasses any type of prophylactic treatment that reduces the incidence of the condition, delays the onset and/or progression of the condition, and/or reduces the symptoms associated with the condition. Thus, the context indicates otherwise, the term "treat," "treating" or "treatment of" (or grammatically equivalent terms) refer to both prophylactic and therapeutic regimens.

As used herein, a "treatment effective amount" is an amount that is sufficient to treat (as defined herein) the subject.

A "diagnostic method", as used herein, refers to a screening procedure that is carried out to identify those subjects that are affected with and/or at risk for a particular disorder.

A "prognostic method" refers to a method used to help predict, at least in part, the course of a disease (e.g., more aggressive or less aggressive). Alternatively stated, a prognostic method may be used to assess the severity of the disease. For example, the screening procedure disclosed herein may be carried out to both identify an affected individual, to evaluate the severity of the disease, and/or to predict the future course of the disease. Such methods may be useful in evaluating the possible benefit of therapeutic treatment, what type of treatment to implement, and the like. In addition, a prognostic method may be carried out on a subject previously diagnosed with a particular disorder when it is desired to gain greater insight into how the disease will progress for that particular subject (e.g., the likelihood that a particular patient will respond favorably to a particular drug treatment, or when it is desired to classify or separate patients into distinct and different sub-populations for the purpose of conducting a clinical trial thereon).

All publications, patent applications, patents, and other references mentioned herein are incorporated by reference in their entirety.

Except as otherwise indicated, standard methods can be used for the production of recombinant and synthetic polypeptides, fusion proteins, antibodies or antigen-binding fragments thereof, manipulation of nucleic acid sequences, production of transformed cells, and the like according to the present invention. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

The present inventors have determined that interaction of DOT1L polypeptide with CALM-AF10 fusion protein is implicated in upregulation of HoxA5 and leukemogenesis. Thus, the present invention provides methods of using the interaction(s) between DOT1L and/or CALM-AF10 and/or HoxA5 as a target for drug discovery.

The invention can be practiced with any DOT1L polypeptide or nucleic acid now known or later discovered. DOT1L nucleic acid and polypeptides have previously been described (see, e.g., U.S. Patent Publication No. 2005-0048634 A1; Feng et al., (2002) Curr. Biol. 12:1052-1058; and Okada et al., (2005) Cell 121:167-78). The yeast homolog of DOT1 was originally identified as a Disruptor Of Telomeric silencing (the protein and nucleic acid sequences of yeast DOT1 can be found at Accession No. NP_010728). The human homolog, designated as hDOT1L (human DOT1-like protein), has been cloned and isolated, and determined to be an HMTase. The sequences of the hDOT1L nucleic acid and protein have been deposited under GenBank accession number AF509504. Only the approximately 360 N-terminal amino acids of hDOT1L share significant sequence similarity with the yeast DOT1. The inventors have further identified DOT1 homologs from *C. elegans* (*C. elegans*, GenBank Accession number NP_510056 and CAA90610), Drosophila (GenBank Accession No. CG10272 and AAF54122), mouse (GenBank Accession No. XP_125730), *Anopheles gambiae* (GenBank Accession No. EM03558), and *Neurospora crassa* (GenBank Accession No. EAA33634) from sequences in public databases. The SAM binding domain among these homologs is conserved (approximately 30-100% amino acid sequence identity and 50-100% amino acid similarity [i.e., identical or conserved amino acids]).

The 2.5 Å resolution structure of a fragment of the hDOT1L protein containing the catalytic domain (amino acids 1-416) has been solved. The atomic coordinates for amino acids 1-416 of hDOT1L have been determined and deposited in the RCSB database under ID code 1 NW3 (see also, Min, et al. (2003) Cell 112:711-723).

In particular embodiments of the invention, the DOT1L polypeptide has H3-K79 specific HMTase activity. By H3-K79 "specific" HMTase activity it is meant that all, or essentially all, of the HMTase activity is directed to H3-K79 (e.g., using a histone or nucleosome substrate).

AF10 polypeptides are also known in the art, see, e.g., human AF10 sequence, GenBank Accession No. AY598745; mouse AF10 sequence, GenBank Accession No. 054826. The present invention can be practiced with any AF10 polypeptide known now or later determined.

The invention can further be practiced with any CALM polypeptide now known in the art or later discovered, see, e.g., GenBank Accession Nos. AAB07762 (human amino acid); U45976 (human mRNA); S36327; CM48748 and S36326 (rat amino acid); X6877 and NM_031728 (rat nucleic acid); M83985, AAA37587 and AAA37586 (mouse amino acid); S27866 (mouse nucleic acid); and XM_595075 and XP_595075 (bovine amino acid); S39150 and XP_595075 (bovine nucleic acid).

The terms "DOT1L polypeptide," "AF10 polypeptide" and "CALM polypeptide" encompass functional fragments of the full-length polypeptides and functional equivalents of either of the foregoing that have substantially similar or substantially identical amino acid sequences (at least about 75%, 80%, 85%, 90%, 95% 98% or more amino acid sequence similarity or identity), where the functional fragment or functional equivalent retains one or more of the functional properties of the native polypeptide.

By "functional" it is meant that the polypeptide (or nucleic acid) has the same or substantially similar activity with respect to one or more of the biological properties of the native polypeptide (or nucleic acid), e.g., at least about 50%, 75%, 85%, 90%, 95% or 98% or more of the activity of the native polypeptide (or nucleic acid).

For example, in representative embodiments, a functional DOT1L polypeptide (including functional fragments and functional equivalents as discussed above) has the same or substantially similar H3-K79 HMTase activity, SAM binding activity, histone and/or nucleosome binding activity, AF10 binding activity, CALM-AF10 fusion protein binding activity, leukemogenic activity and/or any other biological activity of interest as compared with a native DOT1L polypeptide.

Methods of assessing DOT1L binding to histones, nucleosomes, nucleic acids or polypeptides can be carried out using standard techniques that will be apparent to those skilled in the art (see the Examples for exemplary methods). Such methods include yeast and mammalian two-hybrid assays and co-immunoprecipitation techniques.

Other biological activities associated with DOT1L such as H3-K79 HMTase and leukemogenic activity can also be evaluated using standard methods known in the art, for example, as described in the Examples below.

The invention can also be practiced with functional fragments of CALM, AF10, and DOT1L, and functional equivalents thereof. In particular embodiments, functional DOT1L fragments and functional equivalents thereof comprise the catalytic domain comprising the SAM binding domain (optionally comprising adjacent sequences) and nucleic acids encoding the same. Functional DOT1L fragments and functional equivalents comprising the catalytic domain can optionally further comprise the DOT1L positively charged region.

In embodiments of the invention, the functional DOT1L fragment or functional equivalent comprises the DOT1L leucine rich interaction domain with AF10.

In representative embodiments, the functional DOT1L fragment or functional equivalent can comprise the leucine zipper region and/or the coiled coil region.

In still further embodiments, the functional DOT1L fragment or functional equivalent comprises the nuclear export signal and/or nuclear localization signal.

In yet a further embodiment, the functional DOT1L fragment or functional equivalent comprises the N-terminal portion of a DOT1 polypeptide, for example, approximately the N-terminal 10, 20, 30, 40, 50, 60, 70, 80, 90 or 100 amino acids. In other embodiments, the functional fragment is truncated at the N-terminus, e.g., less than about 100, 85, 75, 60, 50, 35, 20, 15, 10 or 5 amino acids are truncated from the N-terminus. In representative embodiments, the functional DOT1L fragment or functional equivalent comprises the N-terminal 10 to 100 amino acids, the N-terminal 10 to 70 amino acids, the N-terminal 20 to 50 amino acids or the N-terminal 20 to 40 amino acids. In other representative embodiments, the N-terminal 5 to 100, to 75 or 15 to 50 amino acids are truncated from the N-terminus functional DOT1L fragment or functional equivalent.

With respect to AF10, in representative embodiments, a functional AF10 fragment or functional equivalent has the same or substantially similar DOT1L binding activity, leukemogenic activity and/or any other biological activity of interest as compared with a native AF10 polypeptide. Further, the functional AF10 fragment or functional equivalent can comprise the OM-LZ domain, e.g., amino acids 719-800 of AF10 [human AF10 sequence, Accession No. AY598745; mouse AF10 sequence, Accession No. 054826], the PHD sequence, the AT sequence, the C-terminal glutamine-rich region and/or the nuclear localization signal.

A functional CALM fragment or functional equivalent has the same or substantially similar leukemogenic activity, HoxA5 gene binding activity and/or any other biological activity of interest as compared with a native CALM polypeptide. In particular embodiments, the functional CALM fragment or functional equivalent comprises the putative CRM1-dependent NES (nuclear exporting signal) sequence at its C-terminus, the ENTH domain, the HoxA5 gene binding domain and/or the clathrin-binding domain.

Those skilled in the art will appreciate that functional fragments and functional equivalents can comprise two or more of the functional regions discussed above.

As used herein, "equivalent" refers to an amino acid sequence that is altered by one or more amino acids. The equivalent may have "conservative" changes, wherein a substituted amino acid has similar structural or chemical properties. In particular, such changes can be guided by known similarities between amino acids in physical features such as charge density, hydrophobicity/hydrophilicity, size and configuration, so that amino acids are substituted with other amino acids having essentially the same functional properties. For example: Ala may be replaced with Val or Ser; Val may be replaced with Ala, Leu, Met, or lie, preferably Ala or Leu; Leu may be replaced with Ala, Val or lie, preferably Val or Ile; Gly may be replaced with Pro or Cys, preferably Pro; Pro may be replaced with Gly, Cys, Ser, or Met, preferably Gly, Cys, or Ser; Cys may be replaced with Gly, Pro, Ser, or Met, preferably Pro or Met; Met may be replaced with Pro or Cys, preferably Cys; His may be replaced with Phe or Gin, preferably Phe; Phe may be replaced with His, Tyr, or Trp, preferably His or Tyr; Tyr may be replaced with His, Phe or Trp, preferably Phe or Trp; Trp may be replaced with Phe or Tyr, preferably Tyr; Asn may be replaced with Gln or Ser, preferably Gln; Gln may be replaced with His, Lys, Glu, Asn, or Ser, preferably Asn or Ser; Ser may be replaced with Gln, Thr, Pro, Cys or Ala; Thr may be replaced with Gin or Ser, preferably Ser; Lys may be replaced with Gin or Arg; Arg may be replaced with Lys, Asp or Glu, preferably Lys or Asp; Asp may be replaced with Lys, Arg, or Glu, preferably Arg or Glu; and Glu may be replaced with Arg or Asp, preferably Asp. Once made, changes can be routinely screened to determine their effects on function.

Alternatively, an equivalent may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE™ software.

As is known in the art, a number of different programs can be used to identify whether a nucleic acid or polypeptide has sequence similarity or identity to a known sequence. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48, 443 (1970), by the search for similarity method of Pearson & Lipman, *Proc. Natl. Acad. Sci. USA* 85, 2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12, 387-395 (1984), preferably using the default settings, or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

The length of the polypeptide fragment is not critical. Illustrative functional fragments comprise at least about 80, 100, 200, 300, 400, 500, 600, 700, 800, 1000, 1200, 1400 or more amino acids (optionally, contiguous amino acids) of a full-length polypeptide, e.g., about 80 to 1400 amino acids, about 100 to 1000 amino acids, about 100 to 700 amino acids, or about 200 to 600 amino acids (optionally, contiguous amino acids) of a full-length polypeptide. The invention also provides nucleic acids encoding the functional fragments. Exemplary nucleic acids encoding functional fragments comprise at least about 250, 300, 400, 500, 600, 700, 800, 1000, 1500, 2000, 2500, 3000, 4000 or more nucleotide bases (optionally, contiguous bases) of a nucleic acid encoding a full-length polypeptide, e.g., about 250 to 4000, about 300 to 3000, about 300 to 2000, about 400 to 2000, or about 600 to 1500 nucleotide bases (optionally, contiguous bases).

The polypeptides can be derived from any species of interest (e.g., mammalian [including but not limited to human, non-human primate such as monkey, mouse, rat, lagomorph, bovine, ovine, caprine, porcine, equine, feline, canine, etc.], insect, yeast, avian, plants, etc.) as well as allelic variations, isoforms, splice variants and the like. The amino acid sequences can further be wholly or partially synthetic.

The terms "DOT1L polypeptide," "AF10 polypeptide" and "CALM polypeptide" encompass fusion proteins (and nucleic acid sequences encoding the same) comprising the polypeptide (including functional fragments). In particular embodiments, the fusion protein is a non-naturally occurring fusion protein and the afore-mentioned terms do not encompass naturally occurring fusion proteins. In this context, the term "naturally occurring fusion protein" includes those associated with pathological states such as MLL-AF10 or CALM- AF10. For example, it may be useful to express the polypeptide as a fusion protein that can be recognized by a commercially available antibody (e.g., FLAG motifs) or as a fusion protein that can otherwise be more easily purified (e.g., by addition of a poly-His tail). Additionally, fusion proteins that enhance the stability of the protein may be produced, e.g., fusion proteins comprising maltose binding protein (MBP) or glutathione-S-transferase. As another alternative, the fusion protein can comprise a reporter molecule. In an exemplary embodiment, a fusion protein can be generated for use in yeast two-hybrid systems (e.g., GAL4-DOT1L fusions), as known in the art.

The term "CALM-AF10 fusion protein" encompasses naturally and non-naturally occurring fusion proteins between AF10 and CALM as well as functional fragments and functional equivalents thereof which retain at least one biological activity of CALM-AF10 such as DOT1L binding, HoxA5 gene binding, leukemogenesis and/or any other biological activity of interest. The AF10 and CALM portions of the fusion protein are as described herein for AF10 and CALM polypeptides. Further, a trifusion of DOT1L/CALM-AF10 can be constructed for use in the methods of the invention.

The present invention can be used in a number of research, diagnostic and/or therapeutic applications. To illustrate, the DOT1L polypeptides, CALM polypeptides, AF10 polypeptides and CALM-AF10 fusion proteins and nucleic acids encoding the same can be used to identify:

compounds that bind to and/or modulate (e.g., increase or decrease) one or more biological activities of CALM, including but not limited to leukemogenic activity and/or any other biological activity of interest;

compounds that bind to and/or modulate (e.g., increase or decrease) one or more biological activities of AF10, including but not limited to leukemogenic activity and/or any other biological activity of interest;

compounds that bind to and/or modulate (e.g., increase or decrease) one or more biological activities of CALM-AF10 including leukemogenic activity, upregulation of HoxA5 promoter activity (e.g., increased transcription of a nucleic acid operatively associated with the HoxA5 promoter, whether native or heterologous) and/or any other biological activity of interest;

compounds that modulate (e.g., increase or decrease) the interaction of DOT1L with AF10 or CALM-AF10;

compounds that modulate (e.g., increase or decrease) the nuclear localization of CALM-AF10;

compounds that modulate (e.g., increase or decrease) H3-K79 methylation of the HoxA5 gene by DOT1L or DOT1L/CALM-AF10;

compounds that modulate (e.g., increase or decrease) DOT1L/CALM-AF10, CALM-AF10 or CALM binding at the HoxA5 gene; and/or compounds that modulate (e.g., increase or decrease) regulation of HoxA5 promoter activity (e.g., transcription of a nucleic acid operatively associated with the HoxA5 promoter, whether native or heterologous) by DOT1L/CALM-AF10, CALM-AF10 or CALM.

compounds that bind and/or down-regulate HoxA5 promoter activity (e.g., reduce HoxA5 gene expression or a chimeric construct comprising the HoxA5 promoter operably associated with a transgene, such as a reporter gene).

The present invention further encompasses methods of identifying compounds for the treatment and/or prevention of leukemia by identifying compounds that bind to and/or modulate the biological activity of a DOT1L polypeptide, CALM polypeptide, AF10 polypeptide, CALM-AF10 fusion protein, DOT1L/CALM-AF10 trifusion protein, modulate HoxA5 promoter activity and/or modulate the interaction of DOT1L, CALM, AF10, CALM-AF10 and/or HoxA5. In particular embodiments, the invention provides methods of identifying compounds for the treatment and/or prevention of T cell acute lymphoid leukemia (T-ALL) or acute myeloid leukemia subtype M0/1 (AML-M0/1).

In representative embodiments, the invention provides a method of identifying a candidate compound for the prevention and/or treatment of leukemia, the method comprising: contacting a DOT1L polypeptide with a CALM-AF10 fusion protein in the presence of a test compound under conditions sufficient for binding of the DOT1L polypeptide to the CALM-AF10 fusion protein; and detecting the level of interaction between the DOT1L polypeptide and the CALM-AF10 fusion protein, wherein a reduction in interaction between the DOT1L polypeptide and the CALM-AF10 fusion protein in the presence of the test compound as compared with the level of interaction in the absence of the test compound indicates that the test compound is a candidate compound for the prevention and/or treatment of leukemia.

The level of DOT1L polypeptide interaction with the CALM-AF10 fusion protein can be evaluated by any suitable method, for example, by determining binding between the DOT1L polypeptide and CALM-AF10 and/or by determining histone H3-K79 methylation of the HoxA5 gene or portion thereof (e.g., all or a functional part of the promoter region, exon 1, exon 2 and/or the intron between exon 1 and exon 2) and/or by determining HoxA5 promoter activity (e.g., when the promoter is operatively associated with the native sequence, a cDNA representing the HoxA5 coding sequence or a heterologous sequence such as a reporter gene). The level of DOT1L polypeptide interaction with the CALM-AF10 fusion protein can also be evaluated by determining nuclear localization of CALM-AF10.

Binding between two or more components can be determined directly or indirectly (e.g., by detecting a biological action or consequence that results from binding of the components).

As used herein, a reporter gene can encode any suitable reporter molecule known in the art, including polypeptides and nontranslated RNA such as RNAi and antisense RNA that result in a detectable change in a cell or organism. In representative embodiments, the reporter molecule is a polypeptide, such as an enzyme (e.g., Green Fluorescent Protein, β-glucuronidase, β-galactosidase, luciferase, etc.).

The invention also provides a method of identifying a candidate compound for the prevention and/or treatment of leukemia, the method comprising: contacting a CALM polypeptide or CALM-AF10 fusion protein with a test compound under conditions sufficient for binding of the test compound to the CALM polypeptide or CALM-AF10 fusion protein; and detecting the level of binding between the test compound and the CALM polypeptide or CALM-AF10 fusion protein, wherein binding of the test compound to the CALM polypeptide or CALM-AF10 fusion protein indicates that the test compound is a candidate compound for the prevention and/or treatment of leukemia.

As another aspect, the invention also provides a method of identifying a candidate compound for the prevention and/or treatment of leukemia, the method comprising: contacting a nucleic acid comprising all or a portion of the HoxA5 gene (e.g., comprising all or a functional part of the promoter region, exon 1, exon 2 and/or the intron between exons 1 and 2) with a CALM polypeptide, AF10 polypeptide, DOT1L polypeptide or CALM-AF10 fusion protein in the presence of a test compound under conditions sufficient for binding of the CALM polypeptide, AF10 polypeptide, DOT1L polypeptide or CALM-AF10 fusion protein to the all or portion of the HoxA5 gene; and detecting the level of interaction of the CALM polypeptide, AF10 polypeptide, DOT1L polypeptide or CALM-AF10 fusion protein with the all or portion of the HoxA5 gene, wherein a reduction in interaction between the CALM polypeptide, AF10 polypeptide, DOT1L polypeptide or CALM-AF10 fusion protein with the all or portion of the HoxA5 gene in the presence of the test compound as compared with the level of interaction in the absence of the test compound indicates that the test compound is a candidate compound for the prevention and/or treatment of leukemia.

Figure 5A:
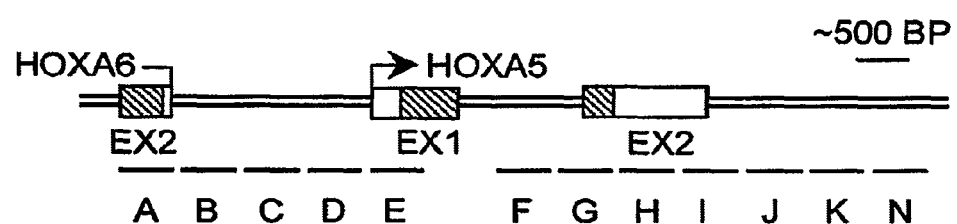
FIGS. 5A-C. CALM-AF10 in association with hDOT1L binds to Hoxa5 both in the promoter and downstream to mediate local H3-K79 methylation. a, Diagram of the Hoxa5 gene locus and amplicons used for ChIP assays. b, ChIP analysis of the location of CALM-AF10 across the Hoxa5 locus in CALM-AF10 transduced and control bone marrow cells. Input=0.5%. c, ChIP analysis of histone modifications in selected regions of the Hoxa5 gene. Cells and antibodies used in the assay are indicated. Input=2%.

Exemplary regions of the HoxA5 gene that can interact with DOT1L/CALM-AF10 are shown in FIG. 5A.

Interaction between the CALM polypeptide, AF10 polypeptide, DOT1L polypeptide or CALM-AF10 fusion protein with the HoxA5 gene or portion thereof can be evaluated by any suitable method, including but not limited to determining binding of the CALM polypeptide, AF10 polypeptide, DOT1L polypeptide or CALM-AF10 fusion protein to the HoxA5 gene or portion thereof and/or by determining H3-K79 methylation of the HoxA5 gene or portion thereof (e.g., all or a functional part of the HoxA5 promoter) and/or by determining HoxA5 promoter activity (e.g., when the promoter is operatively associated with the native sequence, a CDNA representing the HoxA5 coding sequence or a heterologous sequence such as a reporter gene).

In representative embodiments, the method is carried out in a cell-based system, wherein the cells comprise a recombinant nucleic acid comprising a HoxA5 promoter operatively associated with a nucleic acid encoding a reporter molecule (e.g., a polypeptide such as an enzyme). The cell can be a leukemic cell that comprises a CALM-AF10 fusion protein or, alternatively, can be a cell that has been modified to produce a CALM-AF10 fusion protein. One or more candidate compounds can be added to the cell, and binding of CALM-AF10 to HoxA5 as indicated by the level of HoxA5 promoter activity can be evaluated by determining the expression of the reporter molecule (e.g., enzymatic activity).

The invention also provides a method of identifying a candidate compound for the prevention and/or treatment of leukemia, the method comprising: contacting a nucleic acid comprising all or a portion of the HoxA5 gene (as described above) with a DOT1L polypeptide and a CALM-AF10 fusion protein in the presence of a test compound under conditions sufficient for binding of the DOT1L polypeptide and the CALM-AF10 fusion protein to form a complex and for the complex to bind to the HoxA5 promoter; and detecting the level of interaction of the DOT1L/CALM-AF10 fusion protein complex to the HoxA5 promoter, wherein a reduction in interaction of the DOT1L/CALM-AF10 fusion protein complex with the HoxA5 promoter in the presence of the test compound as compared with the level of interaction in the absence of the test compound indicates that the test compound is a candidate compound for the prevention and/or treatment of leukemia.

A DOT1L-CALM-AF10 trifusion protein can be substituted for DOT1L and CALM-AF10 in the foregoing method.

Interaction between the DOT1L/CALM-AF10 complex and HoxA5 gene or portion thereof can be evaluated by any suitable method, including but not limited to determining binding of the complex to the HoxA5 gene or portion thereof or by determining H3-K79 methylation of the HoxA5 gene or portion thereof (e.g., the HoxA5 promoter) or by determining HoxA5 promoter activity (e.g., when the promoter is operatively associated with the native sequence, a cDNA representing the HoxA5 coding sequence or a heterologous sequence such as a reporter gene).

It has previously been observed that HoxA5 is overexpressed in certain leukemias; however, because many genes are dysregulated in cancer, the significance of HoxA5 upregulation was not known. The present inventors have discovered that HoxA5 upregulation is a causal factor in leukemogenesis. Accordingly, the invention also provides methods of identifying a candidate compound for the prevention and/or treatment of leukemia, the method comprising identifying compounds that bind to and/or modulate HoxA5 promoter activity (e.g., by down-regulating expression of the HoxA5 gene or a chimeric construct comprising a HoxA5 promoter operably associated with a transgene, such as a reporter gene). In particular embodiments, the method comprises: contacting a nucleic acid comprising all or a functional part of the HoxA5 promoter region and/or any other region of the HoxA5 gene (e.g., exon 1, exon 2 or the intron between exon 1 and exon2) with a test compound under conditions sufficient for the test compound to bind to the all or functional part of the HoxA5 promoter region and/or the any other region of the HoxA5 gene that is present in the nucleic acid; and detecting the level of binding between the test compound and the all or a functional part of the HoxA5 promoter and/or the any other region of the HoxA5 gene present in the nucleic acid, wherein binding indicates that the test compound is a candidate compound for the prevention and/or treatment of leukemia.

Other representative methods of identifying a candidate compound for the prevention and/or treatment of leukemia comprise: contacting a nucleic acid comprising all or a functional part the HoxA5 promoter region with a test compound under conditions sufficient for HoxA5 promoter activity; and detecting the level of HoxA5 promoter activity, wherein a reduction in HoxA5 promoter activity in the presence of the test compound as compared with the level of HoxA5 promoter activity in the absence of the test compound indicates that the test compound is a candidate compound for the prevention and/or treatment of leukemia. In representative compounds, the test compound binds to the all or functional part of the HoxA5 promoter and/or any other region of the HoxA5 gene (e.g., exon 1, exon 2 and/or the intron between exons 1 and 2) that is present in the nucleic acid. HoxA5 promoter activity can be determined as described herein.

The present invention further provides methods of identifying compounds for the treatment and/or prevention of T-ALL or AML subtypes M0/1 by identifying compounds that bind to and/or modulate the biological activity of a DOT1 polypeptide and/or interaction of DOT1L with AF10.

In a representative embodiment, the invention provides a method of identifying a candidate compound for the prevention and/or treatment of T-ALL or AML subtypes M0/1, the method comprising: contacting a DOT1L polypeptide with a histone or nucleosome substrate comprising histone H3 in the presence of a test compound; detecting the level of H3-K79 methylation of the substrate under conditions sufficient to provide H3-K79 methylation, wherein an inhibition of H3-K79 methylation in the presence of the test compound as compared with the level of H3-K79 methylation in the absence of the test compound indicates that the test compound is a candidate compound for the prevention and/or treatment of T-ALL or AML subtypes M0/1.

The invention further provides a method of identifying a candidate compound for the prevention and/or treatment of T-ALL or AML subtypes M0/1, comprising: contacting a DOT1L polypeptide with AF10; detecting the level of binding between the DOT1L polypeptide and AF10 under conditions sufficient for binding therebetween, wherein a reduction in binding between DOT1L polypeptide and AF10 in the presence of the test compound as compared with the level of binding in the absence of the test compound indicates that the test compound is a candidate compound for the prevention and/or treatment of T-ALL or AML subtypes M0/1.

Methods of assessing binding to polypeptides and nucleic acids can be carried out using standard techniques that will be apparent to those skilled in the art (see the Examples for exemplary methods). Such methods include yeast and mammalian two-hybrid assays and co-immunoprecipitation techniques.

Other activities such as H3-K79 HMTase and leukemogenic activity can also be evaluated using standard methods known in the art, for example, as described in the Examples below.

HoxA5 promoter activity can also be evaluated by any method known in the art, for example, by detecting expression or activity of a reporter gene operably associated with the HoxA5 promoter, by detecting HoxA5 transcripts (e.g., by RT-PCR) and/or the HoxA5 protein product.

The screening methods of the invention can be carried out in a cell-based or cell-free system. As a further alternative, the assay can be performed in a whole animal (including transgenic non-human animals). Further, with respect to cell-based systems, the polypeptide(s) can be added directly to the cell or can be produced from a nucleic acid in the cell. The nucleic acid can be endogenous to the cell or can be foreign (e.g., a genetically modified cell).

Any compound of interest can be screened according to the present invention. Suitable test compounds include small organic compounds (i.e., non-oligomers), oligomers or combinations thereof, and inorganic molecules. Suitable organic molecules can include but are not limited to polypeptides (including enzymes, antibodies and Fab' fragments), carbohydrates, lipids, coenzymes, and nucleic acid molecules (including DNA, RNA and chimerics and analogs thereof) and nucleotides and nucleotide analogs. In particular embodiments, the compound is an antisense nucleic acid, an siRNA or a ribozyme that inhibits production of a target polypeptide.

Small organic compounds (or "non-oligomers") include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, terpenes, porphyrins, toxins, catalysts, as well as combinations thereof.

Oligomers include oligopeptides, oligonucleotides, oligosaccharides, polylipids, polyesters, polyamides, polyurethanes, polyureas, polyethers, and poly (phosphorus derivatives), e.g. phosphates, phosphonates, phosphoramides, phosphonamides, phosphites, phosphinamides, etc., poly (sulfur derivatives) e.g., sulfones, sulfonates, sulfites, sulfonamides, sulfenamides, etc., where for the phosphorous and sulfur derivatives the indicated heteroatom for the most part will be bonded to C, H, N, O or S, and combinations thereof. Such oligomers may be obtained from combinatorial libraries in accordance with known techniques.

Further, the methods of the invention can be practiced to screen a compound library, e.g., a combinatorial chemical compound library (e.g., benzodiazepine libraries as described in U.S. Pat. No. 5,288,514; phosphonate ester libraries as described in U.S. Pat. No. 5,420,328, pyrrolidine libraries as described in U.S. Pat. Nos. 5,525,735 and 5,525,734, and diketopiperazine and diketomorpholine libraries as described in U.S. Pat. No. 5,817,751), a polypeptide library, a cDNA library, a library of antisense nucleic acids, and the like, or an arrayed collection of compounds such as polypeptide and nucleic acid arrays.

The invention also encompasses compounds identified by the screening methods described above.

Further, the invention provides methods of treating a subject afflicted with or at risk for leukemia (e.g., T-ALL or AML subtypes M0/1) by administering a treatment effective amount of an inhibitory nucleic acid (e.g., RNAi such as siRNA) or an antibody (e.g., monoclonal antibody) directed against HoxA5, CALM, AF10, CALM-AF10 and/or DOT1L.

According to embodiments of the present invention, the antibody can be a monoclonal or polyclonal antibody including antibody fragments. The antibody and antibody fragment is not limited to any particular form and can be a bispecific, humanized, or chimerized antibody or antibody fragment and can further be a Fab fragment, single chain antibody, and the like.

Suitable subject for practicing the present invention include avian and mammalian subject, with mammalian subjects including but not limited to humans, non-human primates, mice, rats, sheep, pigs, cattle, goats, rabbits, horses, dogs, cats, and the like.

As still a further aspect, the invention encompasses diagnostic methods for assessing whether a subject has or is at risk for leukemia and/or prognostic methods for predicting the future course of leukemia in a subject by assessing H3-K79 histone methylation of HoxA5, wherein an increase in H3-K79 methylation of HoxA5 as compared with a normal (e.g., non-leukemic) subject is diagnostic of leukemia and/or prognostic of the course of the disease. Optionally, the level of H3-K79 methylation and, optionally, the level of H3-K4 methylation of the HoxA5 gene are determined (e.g., the HoxA5 promoter, exon 1, exon 2 and/or the intron between exon 1 and 2), wherein an increase in H3-K79 methylation and, optionally, a reduction in H3-K4 methylation as compared with a normal (e.g., non-leukemic) subject is diagnostic of leukemia and/or prognostic of the course of the disease.

The invention further provides a method of diagnosing whether a subject has or is at risk for developing leukemia and/or determining the prognosis for the course of the disease, the method comprising determining HoxA5 promoter activity in the subject, where upregulation (i.e., increased activity) of HoxA5 promoter activity as compared with HoxA5 promoter activity in a control (e.g., healthy) subject indicates that the subject has or is at risk for developing leukemia. HoxA5 promoter activity can be determined by any method known in the art. For example, the method can further comprise obtaining a biological sample from the subject and determining the HoxA5 promoter activity in the biological sample (e.g., by increased expression of a nucleic acid operatively associated with the HoxA5 promoter, whether native or heterologous).

One exemplary method of diagnosing whether a subject has or is at risk for developing leukemia and/or determining the prognosis for the course of the disease comprises: obtaining a biological sample comprising the HoxA5 gene from a subject; detecting the level of H3-K79 methylation of the HoxA5 gene in the biological sample; wherein an elevation in H3-K79 methylation of the HoxA5 gene in the biological sample as compared with the level of H3-K79 methylation in a non-leukemic biological sample is diagnostic that the subject has or is at risk of developing leukemia and/or prognostic of the course of the disease in the subject. The method can optionally further include determination of the level of H3-K4 methylation of the HoxA5 gene, wherein a decrease in H3-K4 methylation of the HoxA5 gene in the biological sample as compared with a non-leukemic sample is diagnostic that the subject has or is at risk of developing leukemia and/or prognostic of the course of the disease in the subject.

In representative embodiments, the foregoing diagnostic methods of the invention are practiced as a diagnostic and/or prognostic method for T-ALL or AML subtypes M0/1.

One exemplary method of diagnosing whether a subject has or is at risk for developing T-ALL or AML-M0/1 and/or determining the prognosis for the course of the disease comprises: obtaining a biological sample comprising histones (e.g., nucleosomes) from a subject; detecting the level of H3-K79 methylation in the biological sample; wherein an increase in H3-K79 methylation in the biological sample as compared with the level of H3-K79 methylation in a non-leukemic biological sample is diagnostic that the subject has or is at risk of developing T-ALL or AML-M0/1 and/or prognostic of the course of the disease in the subject. The method can optionally further include determination of the level of H3-K4 methylation, wherein a decrease in H3-K4 methylation in the biological sample as compared with a non-leukemic sample is diagnostic that the subject has or is at risk of developing T-ALL or AML-M0/1 and/or prognostic of the course of the disease in the subject.

According to another representative embodiment, the invention provides a method of diagnosing whether a subject has or is at risk for developing T-ALL or AML-M0/1 and/or determining the prognosis for the course of the disease, the method comprising: obtaining a biological sample comprising histones (e.g., nucleosomes) from a subject; detecting the level of H3-K79 methylation associated with one or more HoxA genes (e.g., the HoxA9 gene) in the biological sample; wherein an increase in HoxA gene-associated H3-K79 methylation (e.g., associated with the HoxA9 gene) in the biological sample as compared with the level in a non-leukemic biological sample is diagnostic that the subject has or is at risk of developing T-ALL or AML-M0/1 and/or prognostic of the course of the disease in the subject. The method can optionally further include determination of the level of H3-K4 methylation associated with one or more HoxA genes (e.g., the HoxA9 gene), wherein a decrease in HoxA gene associated H3-K4 methylation in the biological sample as compared with a non-leukemic sample is diagnostic that the subject has or is at risk of developing T-ALL or AML-M0/1 and/or prognostic of the course of the disease in the subject.

Diagnostic and prognostic methods of the invention can be practiced with any mammalian subject including but not limited to human, non-human primate, cattle, sheep, goat, cat, dog, pig, horse, rat, mouse, rabbit or guinea pig subjects. In particular embodiments, the subject has or is believed to be at risk of developing leukemia. In other embodiments, the subject is an animal model of leukemia.

It will be appreciated by those skilled in the art that the diagnostic and prognostic methods of the invention may not be conclusive and may need to be supplemented with other diagnostic and/or prognostic methods to make a final diagnosis or prognosis.

Any suitable biological sample can be used including cell or tissue samples, umbilical cord samples, blood, plasma or serum samples, urine or fecal samples, mucus or sputum samples, and the like. In particular embodiments, the biological sample is a B cell or bone marrow sample. In other representative embodiments, the biological sample is a histone or nucleosome preparation comprising histone H3 (e.g., obtained from B cells or bone marrow cells). In representative embodiments, cells or tissue are removed from a subject, cultured and histones or nucleosomes prepared from the cultured cells or tissue.

By "non-leukemic biological sample" it is meant a suitable control sample that is indicative of a normal subject (i.e., not having or at risk for developing leukemia). For example, the sample can be isolated from a normal subject or, in some instances (e.g., a nucleosome preparation), can be isolated from cultured cells.

Having described the present invention, the same will be explained in greater detail in the following examples, which are included herein for illustration purposes only, and which are not intended to be limiting to the invention.

Example 1

Experimental Procedures

CALM-AF10 Knockdown in U937 Cells and Transplantation.

DNA encoding 21 bp-shRNA (5'-ATC AGG AGC ACA GAG CTG TGA-3'; SEQ ID NO:3) that targets the junction of CALM and AF10 was subcloned into pMSCV-puro with an H1 RNA promoter. Transduced cells were selected by puromycin (0.5 µg/ml) and cloned by limiting dilution. Knockdown efficiency was evaluated by RT-PCR. Five to ten week old NOD/SCID mice were irradiated (300 rad). After 6 hours, CALM-AF10 knockdown (KD) and vector-transduced (V) U937 cells were intraorbitally injected ($1\times10^7$ cells/mouse, n=6 for each group). Mice were monitored and sacrificed at the terminal stage for histology and FACS analysis. Some mice from KD were sacrificed before the terminal stage for control experiment.

Mouse Bone Marrow Cell Isolation and Transduction.

Four- to ten-week-old C57BL/6 mice were used to harvest bone marrow cells. Hoxa5-deficient bone marrow cells were obtained from 8-10 week old MF1 mice (Jeannotte et al., (1993) *Genes Dev* 7, 2085-96). Mice were treated with 150 mg/kg 5-fluorouracil (5FU) for 5 days before bone marrow cells were harvested. Lin⁻ cells were enriched using EasySep® Mouse Hematopoietic Progenitor Cell Enrichment Kit (Stem cell technology), and used for retroviral transduction. cDNA of CALM-AF10 was cloned from U937 cells by RT-PCR. Wild-type and OM-LZ deletion mutant CALM-AF10 were subcloned into pMSCV-neo in the downstream of a Flag-tag. Retrovirus preparation, transduction, and colony assays were performed as previously described (Okada et al., (2005) *Cell* 121:167-78). In the experiments presented in FIG. 3b, G418 (1 mg/ml) was added to the methylcellulose until the 3rd round to prevent the growth of untransduced cells. Colonies on methylcellulose were picked and further cultured in mFTOC (10% FBS in RPMI1640, 1 mM MEM sodium pyruvate, 1% MEM non-essential amino acid, 10 mM HEPES, pH. 7.3, $5\times10^5$ M 2-mercaptoethanol) with 5 ng/ml mIL-3 (Peprotech). Transduction of DOT1L with Blasticidin-resistant retrovirus was described previously (Okada et al., (2005) *Cell* 121:167-78).

Cell Culture, Transfection, Immunostaining, and Immunoprecipitation.

U937 cells were maintained in RPMI 1640 supplemented with 10% fetal calf serum. 293T or U2OS cell were maintained in Dulbecco's modified Eagle's medium (DMEM) supplemented with 10% fetal calf serum. Transfection was performed by using Fugene6 (Roche). Twenty-four hours after transfection, U2OS cells were fixed with 3% paraformaldehyde and permiabilized with 0.1% Triton X-100 for 5 min. Flag M2 (Sigma) and hDOT1L (Okada et al., (2005) *Cell* 21:167-78) antibodies were used as primary antibodies for immunostaining. DAPI was used for nuclear staining.

For immunoprecipitation, 293T cells were harvested 36 hours after transfection, and washed with ice-cold phosphate-buffered saline (PBS) before being lysed with lysis buffer (50 mM Hepes-KOH [pH 7.9], 420 mM KCl, 0.1 mM EDTA [pH 8.0], 5 mM MgCl2, 20% glycerol, 1 mM DTT, 1 mM phenylmethylsulfonyl fluoride, 1 µg of aprotinin/ml, 0.5 µg of leupeptin/ml, and 0.7 µg of pepstatin/ml). After incubation for 1 hr at 4° C., cells were gently sonicated, and the cell debris was removed by centrifugation at 14,000 rpm for 30 min. Anti-Flag M2 agarose beads (Sigma) were added to 0.5 mg protein extracts, and incubated for 3 hours at 4° C. After five washes with lysis buffer containing 500 mM KCl, the immunoprecipitates were analyzed by Western blotting.

FACS Analysis.

Cells harvested from NOD/SCID mice and the mouse bone marrow cells transduced by CALM-AF10 were incubated for 20 min on ice with CD16/CD32 Fc block (BD Pharmingen) and subsequently stained for 30 min on ice with phycoerythrin-, fluorescein isothiocyanate-, and allophycocyanin-conjugated isotype controls and monoclonal antibodies against human CD45, mouse CD11b, Gr-1, c-kit, B220, CD3, and Ter119 (BD Pharmingen). Cells were then washed with 2% FBS-containing PBS and analyzed using a FACSCalibur (BD Pharmingen). Data collected were analyzed with Summit V3.1 (Cytomation Inc., Fort Collins).

RT-PCR Analysis of Hox Genes, Bmi-1 and CALM-AF10.

Total RNA was isolated from vector-transduced or CALM-AF10-knockdown U937 cells, or colonies of mouse bone marrow cells derived from second and third round of wild-type or mutant CALM-AF10 transduced cells using RNeasy (Qiagen). Up to 1 µg of total RNA was treated with RNase-free DNase I, and applied for reverse transcription using ImProm-II (Promega) according to manufacturer's protocol. Half a microliter of cDNA from the 20 µl RT reaction was used as template for PCR amplification using Platinum Taq Polymerase (Invitrogen), with 33-35 cycles. One tenth of the cDNA was used for β-actin and GAPDH amplification. Primer sequences for Hoxa and Bmi-1 are available upon request. Primer sequences for detection of CALM-AF10 gene were as follows,

```
CALM-AF10-F:
5'-TATACAGCCAGCCTGTCATG-3',    (SEQ ID NO: 4)

CALM-AF10-R:
5'-AGTGGCTGCTTTGCTTTCTC-3'.    (SEQ ID NO: 5)
```

ChIP Assay.

Cell preparation, immunoprecipitation, and PCR were described previously (Okada et al., (2005) *Cell* 121:167-78). Antibodies were obtained as follows; anti-3mK4 (Abcam), anti-2mK9 (Upstate), and anti-2mK79 (Feng et al., (2002) *Curr. Biol.* 12:1052-1058). Primer sequences and detailed PCR conditions are available upon request.

Example 2

Results

CALM-AF10 Fusion Protein is Necessary to Mediate Leukemic Transformation.

We have recently demonstrated that hDOT1L, a histone H3-K79 methyltransferase (Feng et al., (2002) *Curr. Biol.* 12:1052-1058), plays an important role in MLL-AF10-mediated leukemogenesis (Okada et al., (2005) *Cell* 121:167-78). We showed that mistargeting of hDOT1L to the Hoxa9 gene by MLL-AF10 results in H3-K79 methylation and Hoxa9 upregulation which contributes to leukemic transformation (Okada et al., (2005) *Cell* 121:167-78). We further demonstrated that the hDOT1L and MLL-AF10 interaction involves the OM-LZ motif of AF10, required for MLL-AF10-mediated leukemic transformation (DiMartino et al., (2002) *Blood* 99, 3780-5). The fact that the OM-LZ region is retained in the CALM-AF10 fusion protein raises the possibility that hDOT1L may also play an important role in CALM-AF10-mediated leukemia. To address a potential role for hDOT1L in CALM-AF10-mediated leukemia, we first attempted to establish a causal-effect relationship between the CALM-AF10 fusion protein and leukemia.

Previous studies have established that the human monocytic leukemia cell line U937 expresses CALM-AF10 fusion protein (Dreyling et al. (1996) *Proc. Natl. Acad. Sci. USA* 93:4804-9; Kobayashi et al., (1995) *Genes Chromosomes Cancer* 13:217-8). To determine whether CALM-AF10 is relevant to cell proliferation and transformation, we performed CALM-AF10 knockdown in U937 cells using a vector-based RNAi approach (Okada et al., (2005) *Cell* 121:167-78). Results shown in FIG. 1a indicate that we are able to generate a stable U937 derivative cell line with significant CALM-AF10 knockdown (compare lanes 1 and 2). Compared to the vector-transduced control (V), the knockdown (KD) cells not only proliferated slower in liquid RPMI media (FIG. 1b), but also resulted in fewer and smaller colonies when cultured on methylcellulose (FIG. 1c). This data suggests that knockdown of CALM-AF10 affects both cell proliferation and transformation in vitro.

Figure 1F:
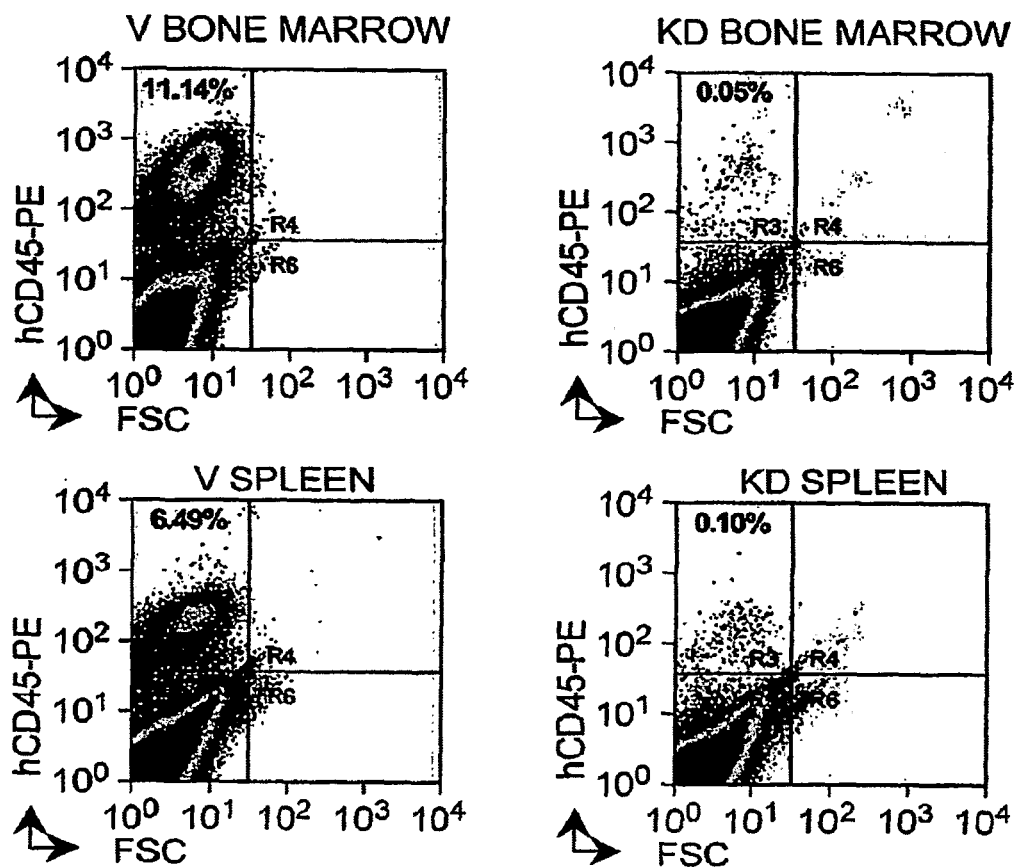

To evaluate the role of CALM-AF10 in vivo, we transplanted $1 \times 10^7$ knockdown and control cells into NOD/SCID mice. Results shown in FIG. 1d demonstrate that CALM-AF10 knockdown prolonged the survival time of the transplanted mice. Histological analysis of the mice transplanted with the vector-transduced control cells revealed infiltration of leukemic cells in multiple organs at the terminal stage (FIG. 1e, upper panels). In contrast, leukemic cells were barely detectable in the organs of the mice transplanted with CALM-AF10 knockdown cells when analyzed on the same day of post-transplantation (FIG. 1e, lower panels). FACS analysis of cells isolated from bone marrow and spleen revealed that transplantation with CALM-AF10 knockdown cells resulted in a significantly lower percentage of human cells when compared to control (0.05% verses 11.14% in bone marrow, 0.10% verses 6.49% in spleen) even though equal numbers of cells were transplanted (FIG. 1f). Collectively, the above results support that the CALM-AF10 fusion protein contributes to cellular proliferation and transformation of leukemic cells in vitro and in vivo.

CALM-AF10-Mediated Leukemic Transformation Depends on Functional hDOT1L.

Figure 2A:
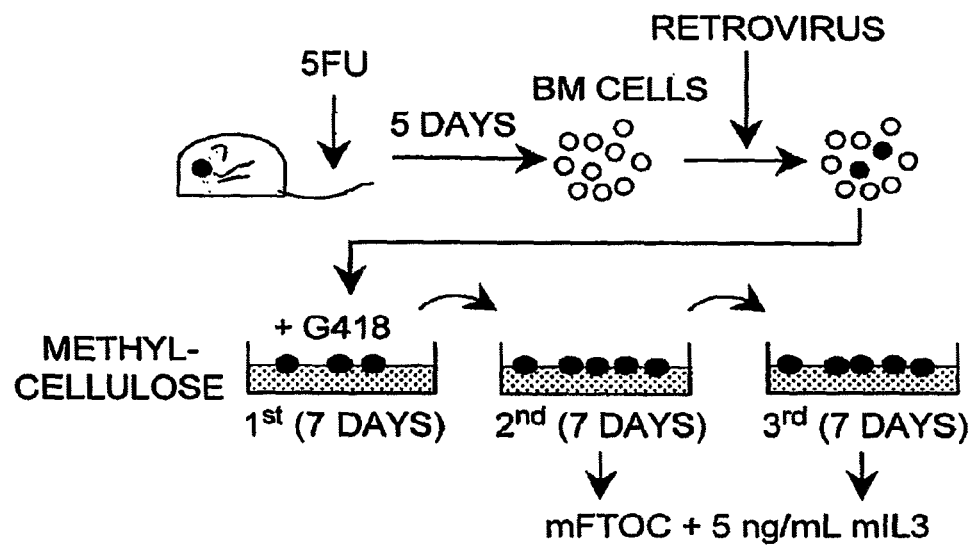
FIGS. 2A-F. Expression of CALM-AF10 is sufficient to cause mouse bone marrow cell transformation and hDOT1L plays an important role in this process. a, Schematic representation of the retroviral transduction procedures. b, Expression confirmation of the transduced genes by RT-PCR. U937 cells serve as a positive control. GAPDH serves as a control for equal input RNA in RT-PCR. c, Serial colony plating assay of bone marrow cells transduced by wild-type and mutant CALM-AF10 with vector control. Presented is the average colony numbers with standard deviations of three independent experiments. The p value of the third round colony numbers between the wild-type and the OM-LZ deletion mutant is presented. d, Growth curve of the transduced cells in mFTOC culture. e, Immunophenotyping by FACS of CALM-AF10 transformed cells. The cell surface markers used in the analysis are indicated. f, Diagram of the 2nd transduction procedure (left panel), and the effect of wild-type and catalytic-deficient hDOT1L on colony formation of CALM-AF10 transformed cells (right panel).
Figure 2B:
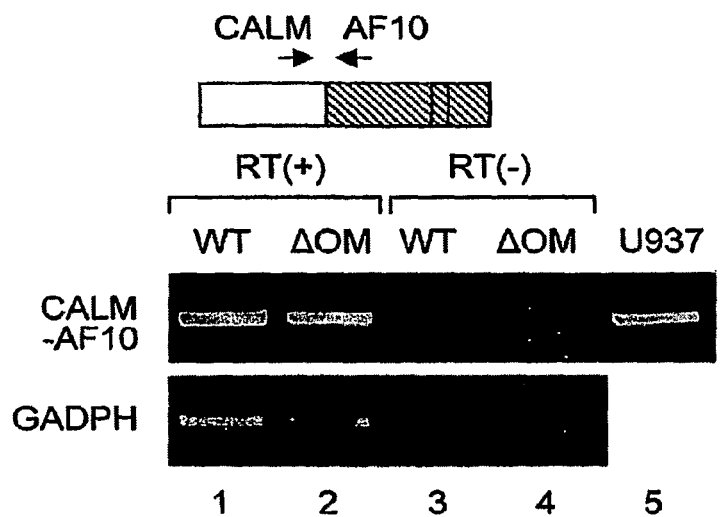
Figure 2C:
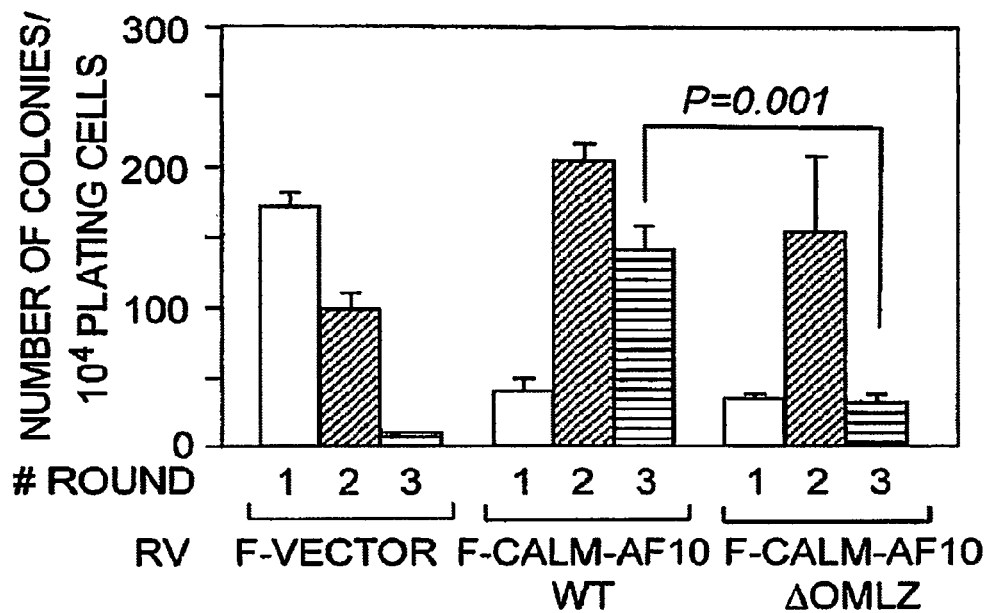
Figure 2D:
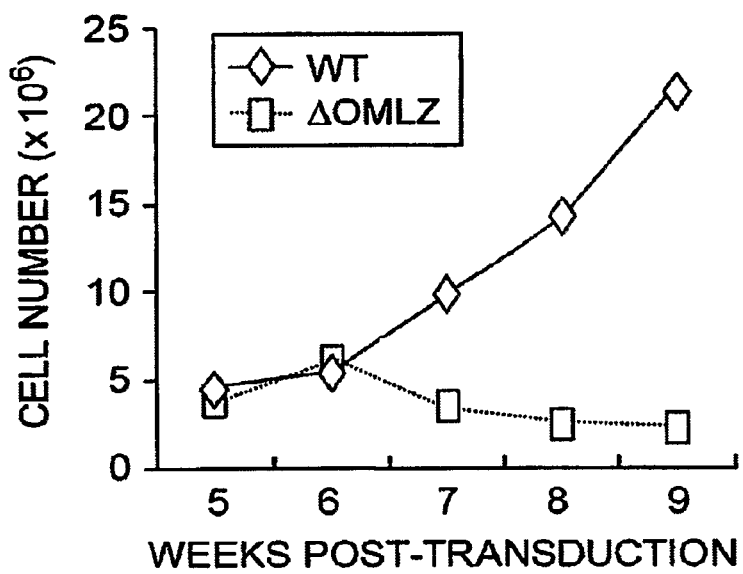
Figure 2E:
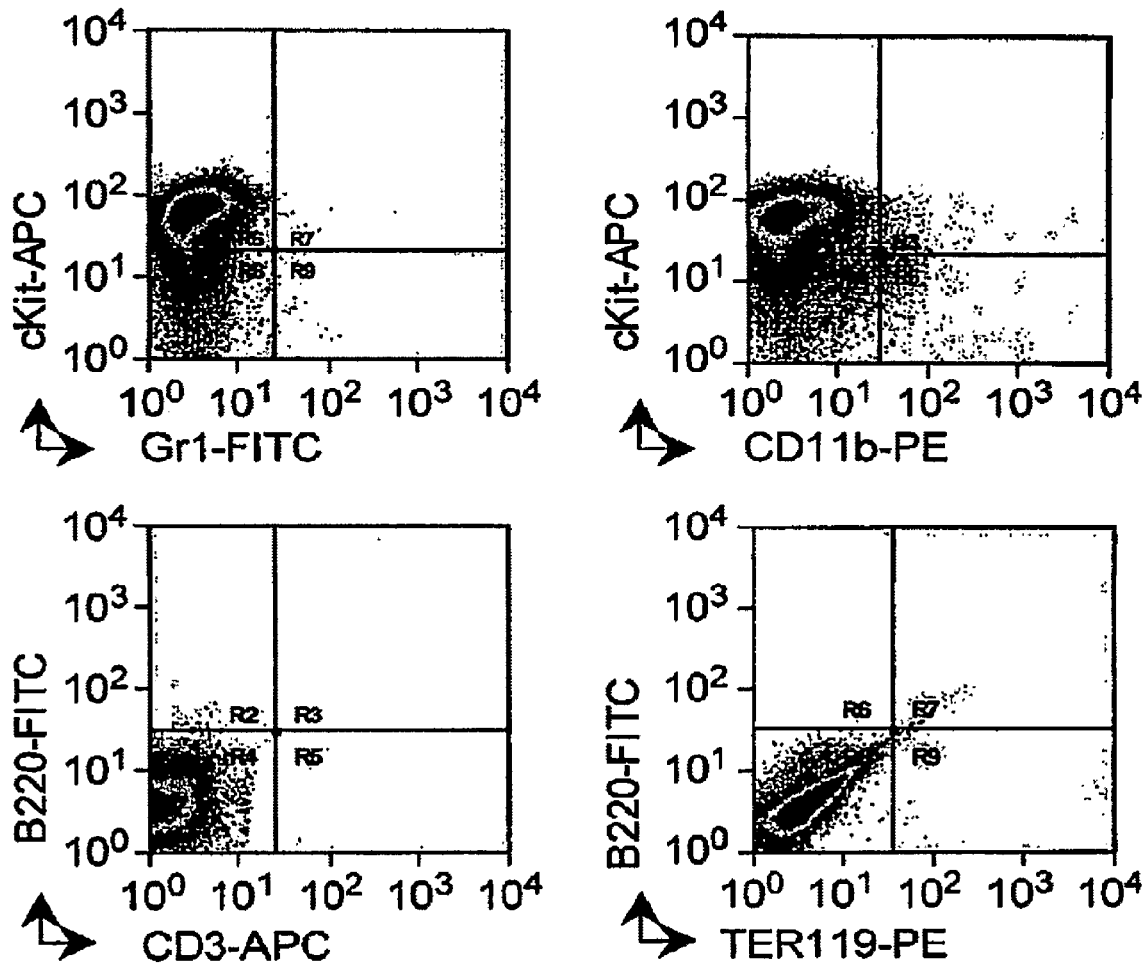
Figure 2F:
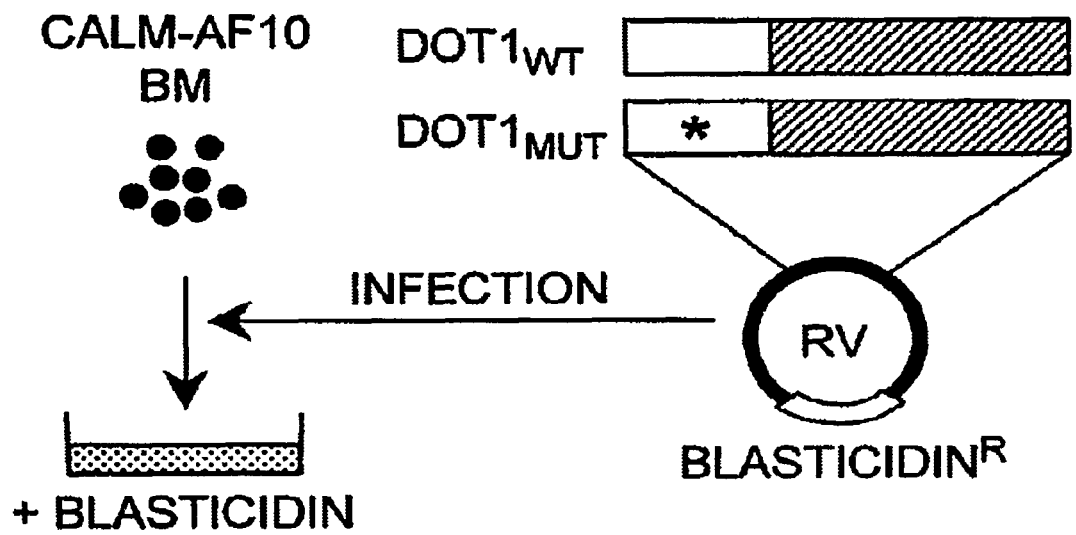
Figure 2F:
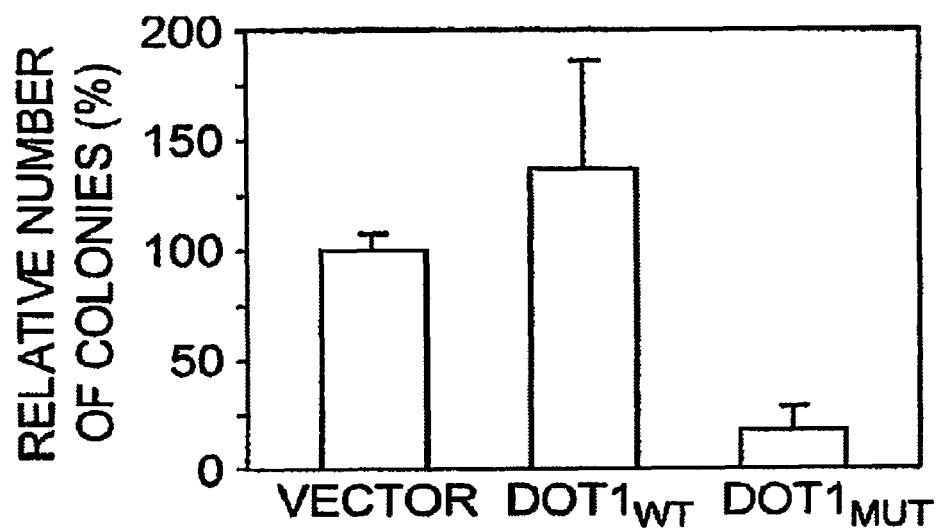
Figure 6A:
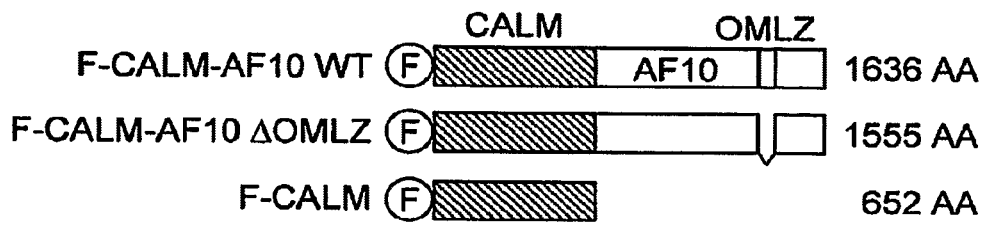
FIGS. 6A-B. CALM-AF10 and hDOT1L interaction is mediated by the OM-LZ region of AF10. a, Diagram of the constructs used in transfection. b, Co-immunoprecipitation of CALM-AF10 and hDOT1L in 293T cells. Transfected cells were harvested 36 hours post-transfection. Total cell extracts were prepared with lysis buffer containing 420 mM KCl. M2 agarose beads were used for immunoprecipitation, and the beads were washed with lysis buffer containing 500 mM KCl. The result was analyzed by Western blotting using hDOT1L (top panel) and Flag (bottom panel) antibodies. In: Input, S: Supernatant, IP: Immunoprecipitate.
Figure 6B:
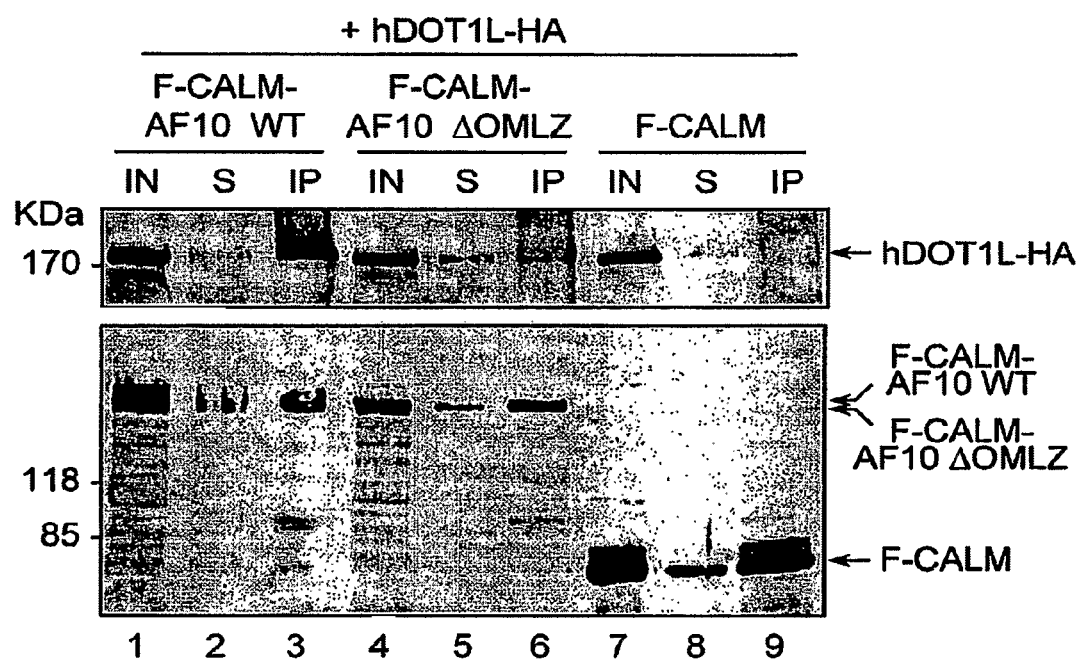

We next analyzed whether expression of CALM-AF10 is sufficient to cause bone marrow cell transformation. For this purpose, a methylcellulose colony serial plating assay was used (FIG. 2a). To address the role of hDOT1L in CALM-AF10-mediated bone marrow transformation, we first established that hDOT1L can interact with CALM-AF10 and the interaction is dependent on the OM-LZ region of AF10 (FIG. 6). Then, we performed the colony serial plating assay by transduction of mouse bone marrow cells with wild-type or a deletion CALM-AF10 mutant that lacked the hDOT1L interaction region OM-LZ. RT-PCR analysis confirmed expression of both fusion proteins in cells derived from the second round of colonies (FIG. 2b, lanes 1 and 2). Although the colony numbers did not increase in the third round of plating when compared with the second round in bone marrow cells expressing CALM-AF10 (FIG. 2c, middle columns), the cells were able to proliferate continuously in mFTOC (mouse fetal thymus organ culture) media supplemented with mIL-3 for more than 6 months (FIG. 2d and data not shown). In contrast, cells that expressed the OM-LZ deletion mutant of CALM-AF10 did not generate a significant number of third round colonies in the methylcellulose assay and did not continue to proliferate in mFTOC media after 6 weeks of culturing (FIGS. 2c and 2d). FACS analysis of the cells transformed by CALM-AF10 indicate that the cells express c-Kit, but none of the other lineage-specific markers such as Gr-1, CD11b, B-220, CD3, and TER-119 (FIG. 2e), indicating that these cells are likely early progenitor bone marrow cells that have not committed to any hematopoitic cell lineages. Based on these results, we conclude that expression of CALM-AF10 fusion protein is sufficient to transform progenitor bone marrow cells and that the hDOT1L interaction region is required for the transformation capacity of CALM-AF10. The fact that the hDOT1L interaction region of AF10 is required for the transformation capacity of CALM-AF10 strongly suggests that hDOT1L plays an important role in CALM-AF10-mediated leukemogenesis. To further demonstrate the role of hDOT1L mediated H3-K79 methylation in proliferation and leukemic transformation by CALM-AF10, we expressed wild-type and mutant hDOT1L defective in its H3-K79 methyltransferase activity in CALM-AF10 transformed bone marrow cells. We then analyzed their effect on colony formation on methylcellulose. Results shown in FIG. 2f indicate that expression of the wild-type hDOT1L enhanced the colony formation, while expression of the mutant hDOT1L strongly suppressed the colony forming capacity of the CALM-AF10 expressing cells (FIG. 2f). Therefore, we conclude that hDOT1L and its associated H3-K79 methyltransferase activity plays an important role in CALM-AF10-mediated leukemic transformation.

CALM-AF10-Mediated Leukemic Transformation Involves Hoxa5 Upregulation.

Figure 3A:
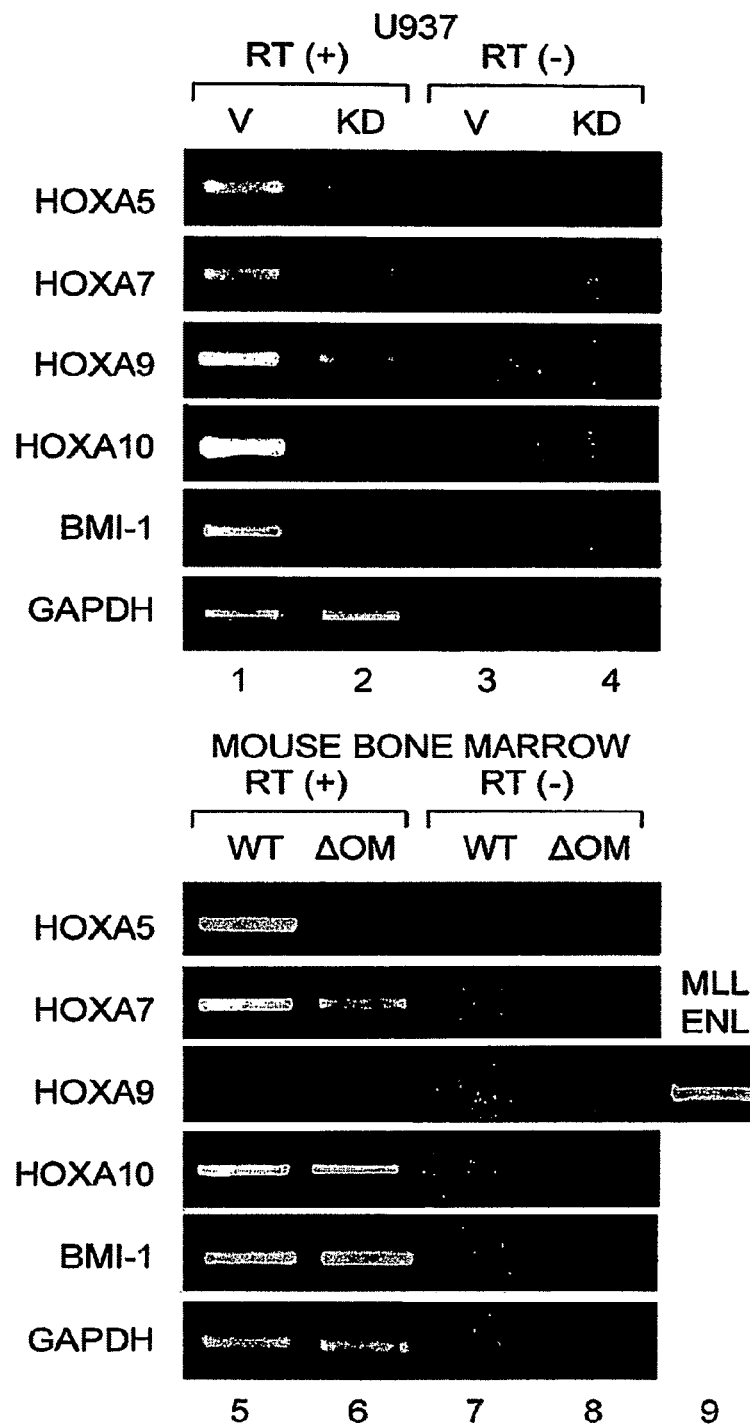
FIGS. 3A-B. Hoxa5 is involved in leukemic transformation by CALM-AF10. a, Left panel, RT-PCR analysis of the expression of late Hoxa genes and Bmi-1 in wild-type and CALM-AF10 knockdown U937 cells. Right panel, RT-PCR analysis of expression of late Hoxa genes and Bmi-1 in mouse bone marrow cells derived from second round colonies, and transduced by wild-type and OM-LZ deletion CALM-AF10 mutants. Lack of detectable signal for Hoxa9 is not due to primer failure as the same primers detected Hoxa9 expression in MLL-ENL transduced cells (lane 9). b, Hoxa5 knockout attenuates the transformation capability of CALM-AF10, but has no effect on that of MLL-AF10. Serial colony plating assays were performed as that in FIG. 2a. Presented is the average colony numbers with standard deviations of three independent experiments. Due to embryonic lethality of Hoxa5 knockout in C57B6 strain, bone marrow cells used in the assays were derived from Hoxa5 knockout and wild-type littermates of MF1 strain (Jeannotte et al., (1993) *Genes Dev* 7, 2085-96).

Having established the role of hDOT1L in CALM-AF10-mediated leukemic transformation, we attempted to identify the relevant target genes. cDNA microarray studies have revealed that overexpression of late Hoxa genes and Bmi-1 is a characteristic of leukemias involving CALM-AF10 and some MLL-fusion proteins (Dik et al., (2005) *Leukemia* 19:1948-57; Drabkin et al., (2002) *Leukemia* 16:186-95; Souler et al., (2005) *Blood* 106:274-86). In particular, overexpression of Hoxa9 has been demonstrated to be crucial for leukemias involving MLL-ENL and MLL-AF10 fusion proteins (Okada et al., (2005) *Cell* 121:167-78) (Ayton et al., (2004) *Genes Dev* 17:2298-307. 24:617-28; Zeisig et al., (2004) *Mol. Cell. Biol.* 24:617-28). To understand the molecular mechanism by which hDOT1L and H3-K79 methylation contribute to leukemogenesis by CALM-AF10, we analyzed late Hoxa genes and Bmi-1 expression by RT-PCR. Results shown in FIG. 3a (compare lanes 1 and 2) indicate that knockdown CALM-AF10 in U937 cells resulted in decreased expression of late Hoxa genes and Bmi-1 (FIG. 3a, left panel). Consistent with this result, overexpression of CALM-AF10 in mouse bone marrow cells resulted in activation of these genes (FIG. 3a, right panel). The hDOT1L interaction region did not appear to have a role in Bmi-1 upregulation although it did affect expression of late Hoxa genes (FIG. 3a, compare lanes 5 and 6). Interestingly, Hoxa5 was significantly upregulated in mouse bone marrow cells transduced by CALM-AF10 when compared with cells transduced by the OM-LZ deletion mutant (FIG. 3a, compare lanes 5 and 6), suggesting that hDOT1L plays a role in Hoxa5 upregulation. Given that the expression level of Hoxa9 was undetectable in the CALM-AF10 transformed cells, Hoxa5 upregulation may play a key role in the transformation process. To determine whether Hoxa5 is necessary for CALM-AF10-mediated leukemic transformation, we performed colony replating assays using bone marrow cells isolated from Hoxa5 knockout mice. In parallel, we also analyzed the effect of Hoxa5 knockout on the transformation capability of MLL-AF10. Result shown in FIG. 3b indicate that while CALM-AF10 can transform bone marrow cells derived from the wild-type mice, as evidenced by increased colony numbers in the third round of plating, it fails to transform bone marrow cells deficient for Hoxa5. In contrast, Hoxa5 knockout does not affect the transformation capability of MLL-AF10. Based on these results, we conclude that Hoxa5 upregulation is critical for CALM-AF10 mediated leukemic transformation.

Nuclear Localization of CALM-AF10 Depends on its Ability to Interact with hDOT1L.

Figure 4A:
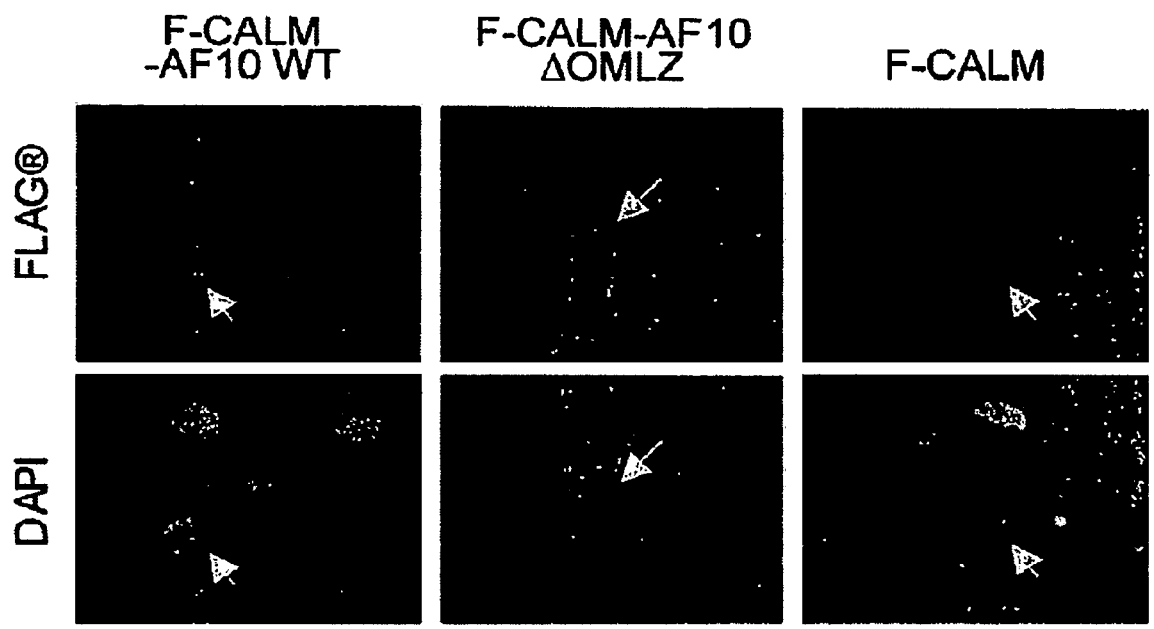
FIGS. 4A-E. hDOT1L retains CALM-AF10 in the nucleus. a, Subcellular distribution of wild-type and OM-LZ deletion mutants, Flag-CALM-AF10, and CALM in U2OS cells. Transfected cells (red, upper panel) are indicated with arrows. Nuclei are stained by DAPI (lower panel). b, Analysis of nuclear staining by Flag antibody with confocal microscopy. Bar=10 mm. c, Immunofluorescent staining of U2OS cells co-transfected with hDOT1L (green, upper panel) and Flag-CALM-AF10 (red, middle panel). Transfected cells are indicated with arrows. Nuclei are stained by DAPI (lower panel). d, Quantification of the cells presented in (c). N: cells expressed in the nucleus. C: cells expressed in the cytoplasm. e, Confocal microscopy analysis of nuclear localization of hDOT1L and CALM-AF10 when co-expressed. Presented are the two staining patterns observed. The pattern shown in the lower panels with more dots is predominant (~80%). Bar=10 mm.
Figure 4B:
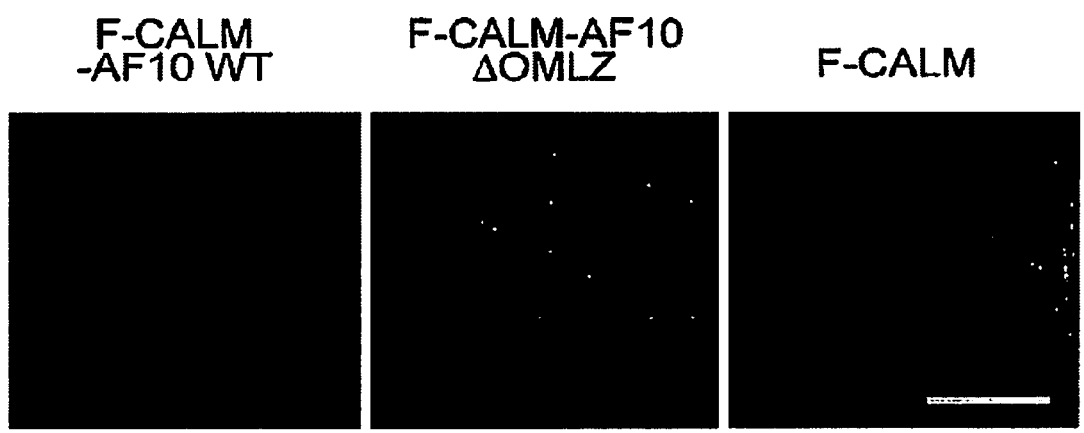
Figure 4C:
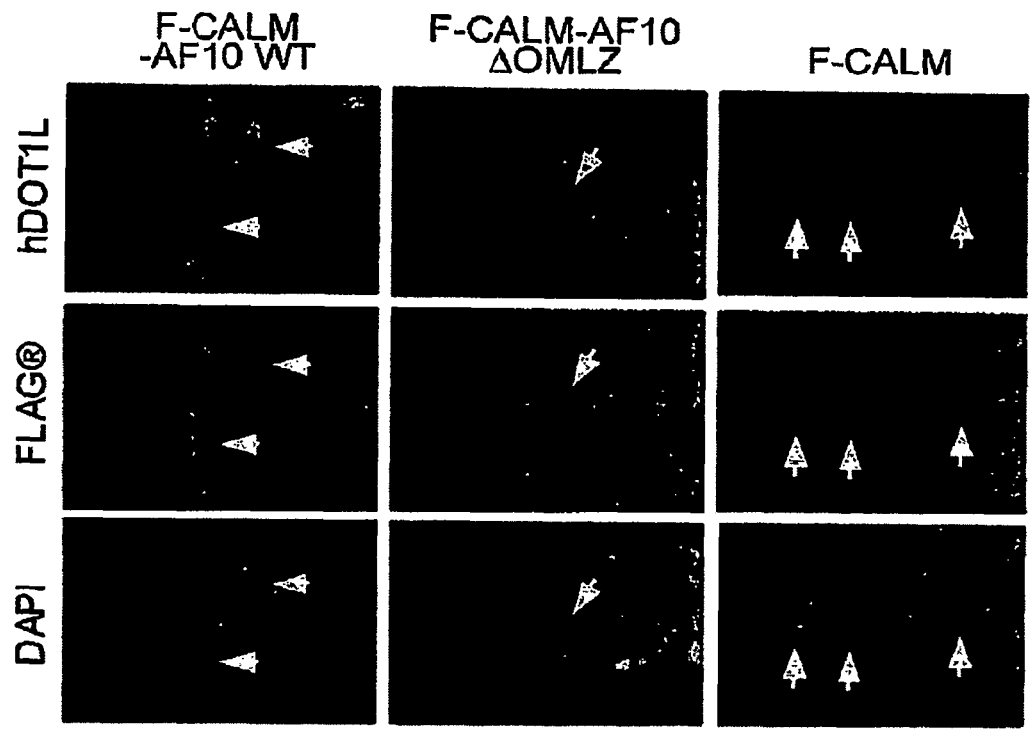
Figure 4D:
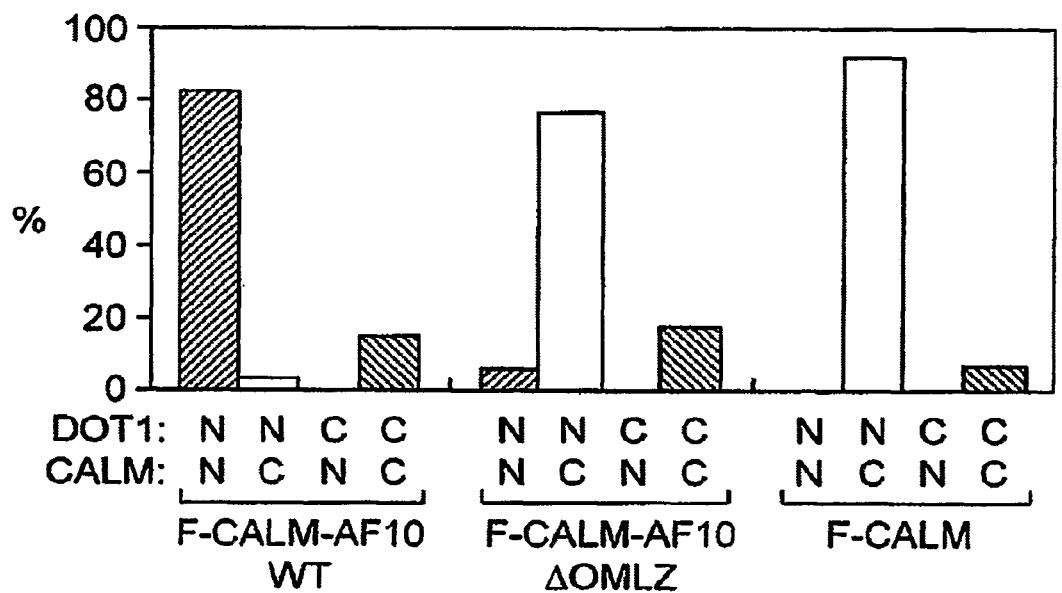
Figure 4E:
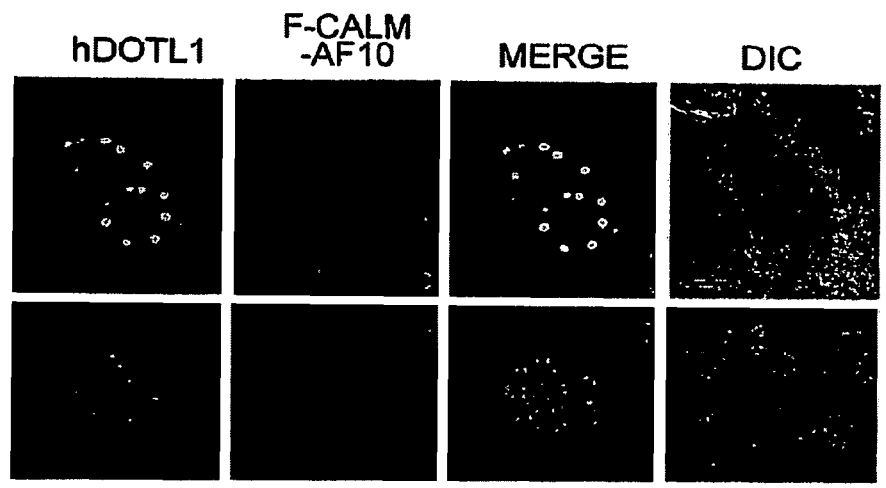
Figure 7A:
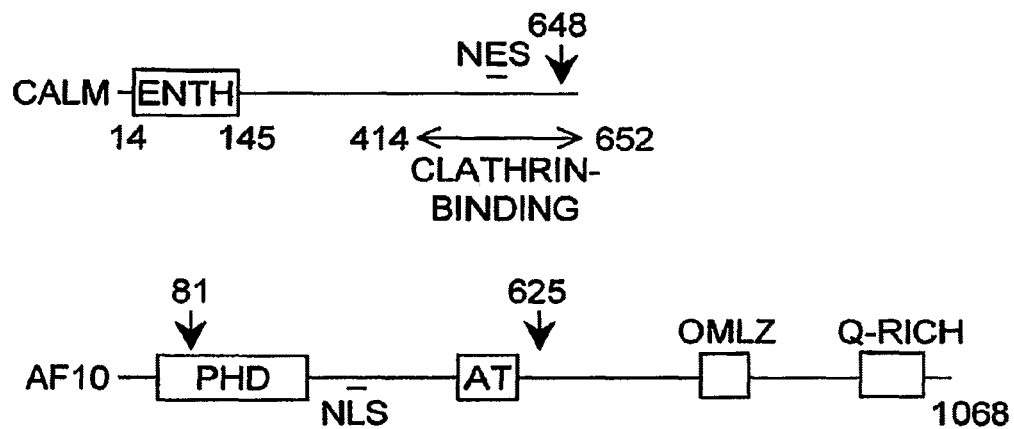
FIGS. 7A-B. a, Schematic representation of CALM and AF10 proteins. Potential functional motifs, including NES and NLS are indicated. Red arrows indicate the major breakpoint for the CALM-AF10 fusion present in U937 cells. The green arrow indicates breakpoint of AF10 in MLL-AF10 fusion. Numbers represent amino acid position. b, Alignment of a putative NES sequence in CALM. This sequence is conserved in AP180, an endocytotic accessory protein similar to CALM.
Figure 7B:
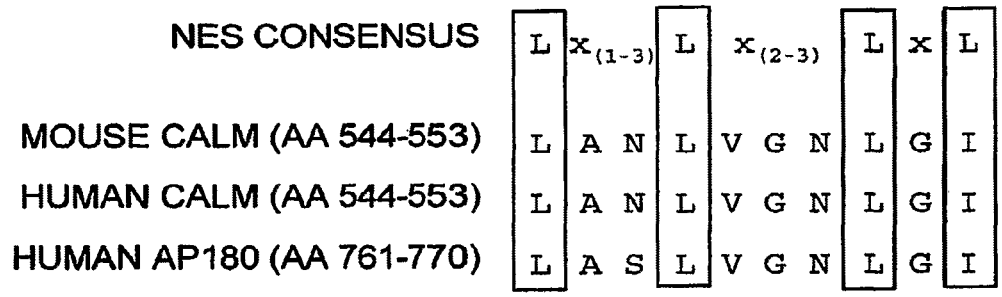

CALM is a cytoplasmic protein known to function in clathrin assembly (Tebar et al., (1999) *Mol. Biol. Cell.* 10:2687-702; Meyrholz et al., (2005) *Traffic* 6:1225-34). It contains a putative CRM1-dependent NES (nuclear exporting signal) sequence at its C-terminus, which is retained in the CALM-AF10 fusion protein (Vecchi et al., (2001) *J. Cell. Biol.* 153:1511-7). (FIG. 7). On the other hand, AF10 is a nuclear protein with its NLS (nuclear localization signal) retained in the CALM-AF10 fusion protein (FIG. 7). Depending on the subcellular localization, CALM-AF10 may directly or indirectly contribute to Hoxa5 upregulation. To determine the subcellular localization of CALM-AF10, we transfected plasmid DNA that encodes Flag-tagged CALM-AF10 into U2OS cells. In parallel, we also transfected two constructs encoding CALM-AF10 with deletion on the OM-LZ region and Flag-tagged CALM. Immunofluorescent staining revealed that most of the overexpressed CALM-AF10 proteins exhibited cytoplasmic distribution (FIG. 4a). However, nuclear distribution in wild-type, but not in mutant, CALM-AF10 transfected cells is also noticeable (FIGS. 4a, b). In contrast, CALM exhibited a mesh-like cytoplasmic distribution (FIG. 4a) which is characteristic of clathrin-related proteins (Tebar et al., (1999) *Mol Biol. Cell* 10:2687-702). Interestingly, when CALM-AF10 is co-expressed with hDOT1L, CALM-AF10 becomes localized to the nucleus (FIGS. 4c, 4d, left columns). High resolution analysis of the proteins indicates that they colocalize in the nucleus (FIG. 4e). Importantly, this change in CALM-AF10 localization depends on its ability to interact with hDOT1L since co-expression of hDOT1L with a CALM-AF10 mutant that lacks the OM-LZ region has no effect on the localization of the fusion protein (FIGS. 4c, 4d, middle columns). In addition, hDOT1L did not affect CALM localization (FIGS. 4c, 4d, right panels). These results strongly suggest that hDOT1L interacts with and retains CALM-AF10 in the nucleus. The results also suggest that the nuclear CALM-AF10 observed in FIGS. 4a and 4b is likely due to interaction with endogenous hDOT1L.

Upregulation of Hoxa5 is Concomitant with CALM-AF10 Binding and H3-K79 Methylation.

Figure 5B:
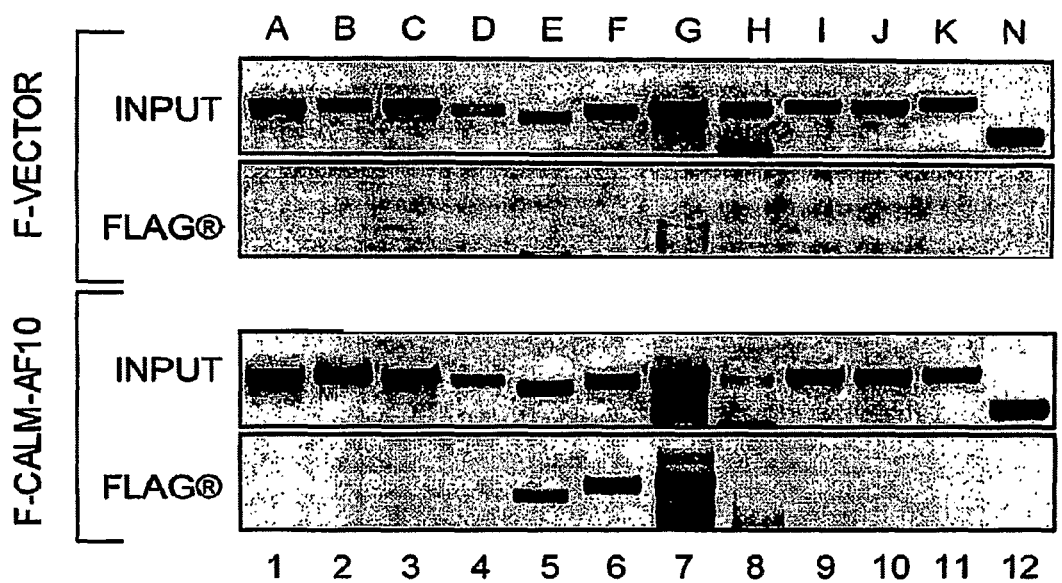
Figure 5C:
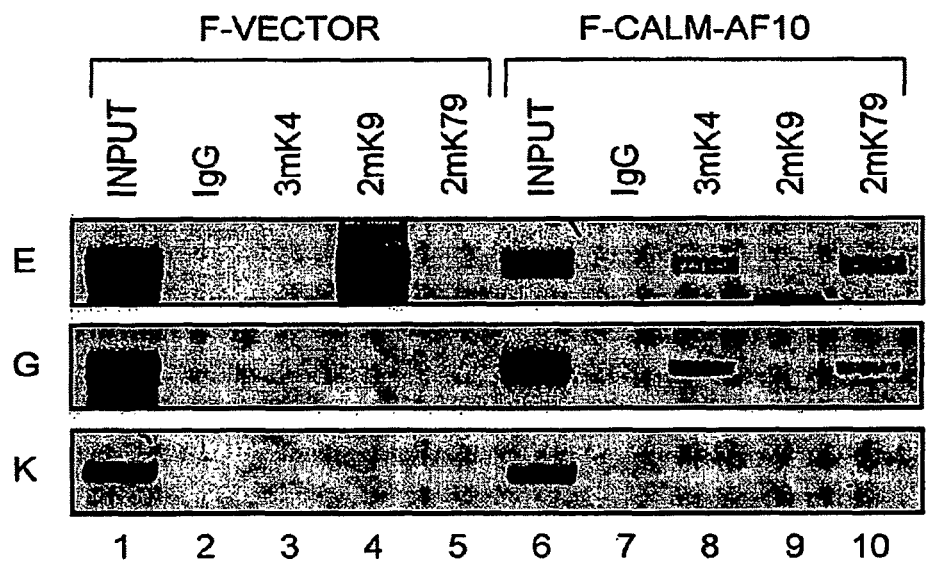

The fact that CALM-AF10 can localize to the nucleus and interact with hDOT1L raises the possibility that Hoxa5 might be a direct target of CALM-AF10. To address this possibility, we analyzed binding of CALM-AF10 across the entire Hoxa5 gene by ChIP using the CALM-AF10 transformed cells described in FIG. 2. Results shown in FIG. 5b demonstrate that the fusion proteins bind to a region covered by amplicons e-g (FIG. 5b, lanes 5-7). The observed binding is specific, as no signal is observed in a parallel ChIP experiment using cells transduced by an empty vector. Given that CALM-AF10 interacts with the H3-K79 methyltransferase hDOT1L, we expect the CALM-AF10 binding sites to be enriched for H3-K79 methylation in the CALM-AF10 transformed cells. ChIP results presented in FIG. 5c demonstrate that H3-K79 methylation correlates with the presence of CALM-AF10 in the transformed cells but not in the control cells (compare lanes 5 and 10). Consistent with the notion that H3-K4 methylation correlates with gene activation while H3-K9 methylation correlates with gene repression, H3-K9 methylation was observed at the Hoxa5 gene promoter when it is silenced in non-transformed bone marrow cells (FIG. 5c, lane 4), while H3-K4 methylation was observed when the gene is activated in CALM-AF10 transformed cells (FIG. 5c, lane 8). All the ChIP signals are specific as they are not present in a control region covered by amplicon k. These results are consistent with a model in which CALM-AF10, in association with hDOT1L, is targeted to the Hoxa5 gene. This targeting results in upregulation of the Hoxa5 gene which in turn contributes to leukemic transformation.

Figure 3B:
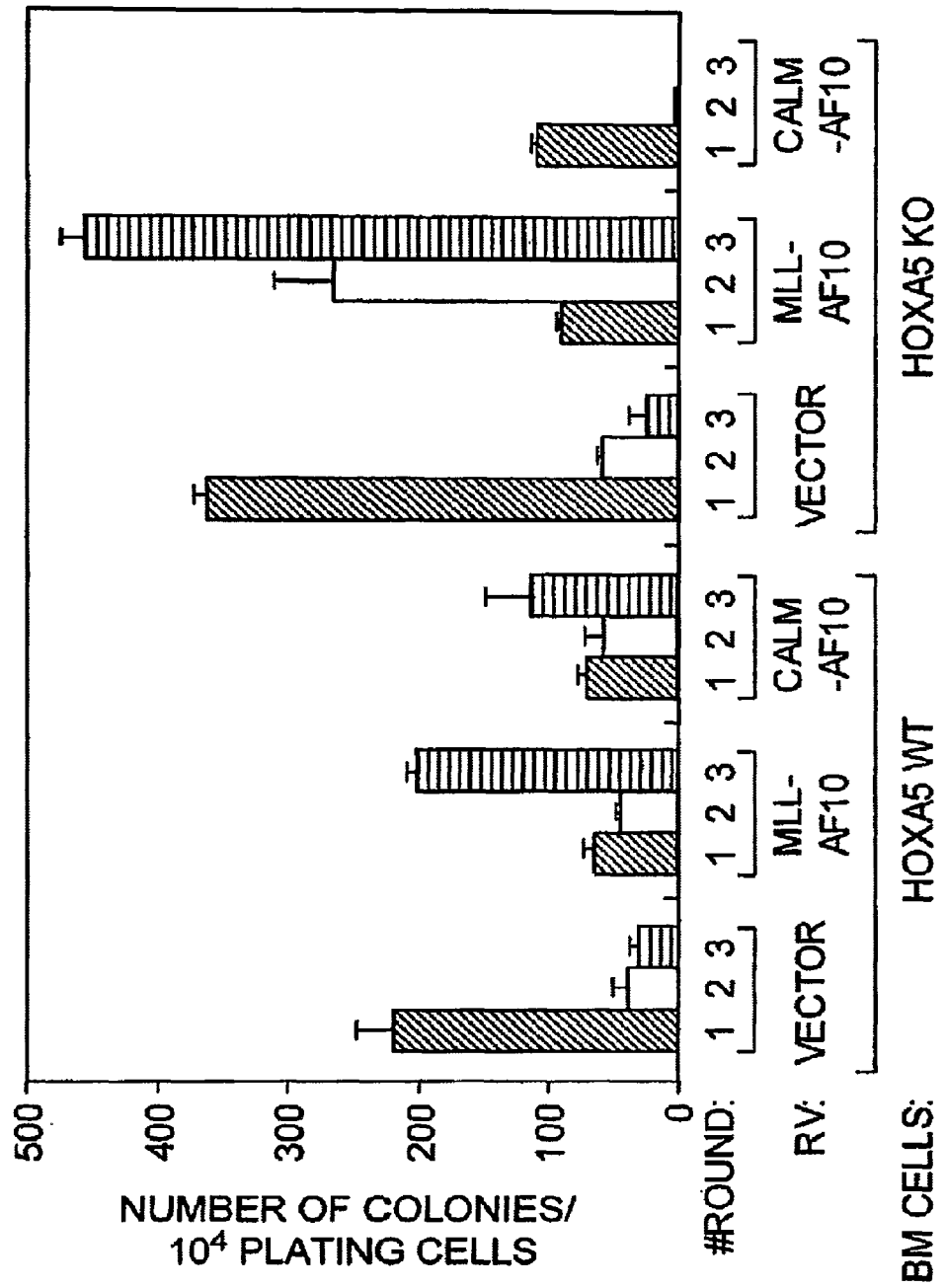

Identification of a chromosomal translocation that produces CALM-AF10 fusion in certain leukemia patients has provided circumstantial evidence indicating CALM-AF10 might possess oncogenic capability. In this study, using bone marrow transformation and transplantation assays, we demonstrate that CALM-AF10 fusion is both necessary and sufficient for leukemogenesis (FIGS. 1 and 2). In addition, we provide two pieces of evidence that support a role for hDOT1L in CALM-AF10 mediated leukemic transformation. First, CALM-AF10 lacking the hDOT1L interaction domain loses its transformation capability (FIG. 2c). Secondly, overexpression of an enzymatically inactive form of hDOT1L suppressed proliferation of CALM-AF10 transformed cells (FIG. 2f). Furthermore, we demonstrated that hDOT1L contributes to CALM-AF10-mediated leukemic transformation by preventing nuclear export of CALM-AF10 and by methylation of H3-K79 at the Hoxa5 gene which contributes to its activation. Finally, we showed that Hoxa5 is required specifically for CALM-AF10 mediated leukemic transformation because bone marrow cells derived from Hoxa5 null mice, while not affecting transformation by MLL-AF10, cannot be transformed by CALM-AF10 (FIG. 3b). Thus, our studies not only establish CALM-AF10 as a cause of leukemic transformation, but also reveal Hoxa5 and hDOT1L as important players in a leukemogenesis process that involves CALM-AF10 fusion.

Figure 8:
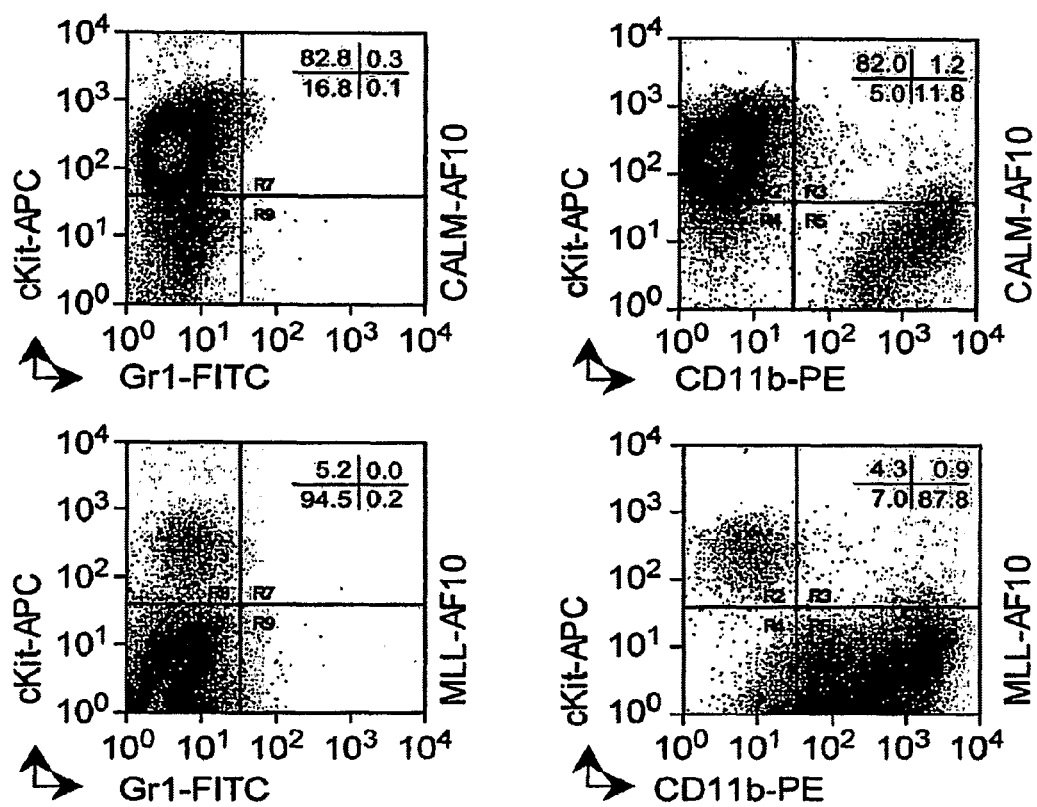
FIG. 8. FACS analysis demonstrating the immunophenotypic differences between CALM-AF10 and MLL-AF10-transduced bone marrow cells. Cells derived from second round colonies of wild-type Hoxa5 bone marrow cells were stained with c-Kit, Gr1, and CD11b antibodies before FACS analysis.

We have previously demonstrated that hDOT1L also contributes to leukemogenesis by MLL-AF10 (Okada et al., (2005) Cell 121:167-78). Although leukemogenesis mediated by MLL-AF10 and CALM-AF10 both involve hDOT1L and Hox gene activation, the underlying mechanisms are not the same. Unlike CALM-AF10, Hoxa5 does not appear to play a key role in MLL-AF10-mediated leukemic transformation (FIG. 3b). Instead, Hoxa9 upregulation through hDOT1L-mediated H3-K79 methylation appears to be a key event in MLL-AF10-mediated leukemic transformation (Okada et al., (2005) Cell 121:167-78). It worth noting that while Hoxa9 overexpression has been observed in a number of leukemias, its overexpression is not always required for leukemic transformation (So et al., (2004) Blood 103:3192-9). This highlights the importance of distinguishing overexpressed Hoxa genes necessary for leukemic transformation from those not essential for transformation. A second difference lies in their distinct immunophenotypes. While CALM-AF10 transformed bone marrow cells are mainly lineage-uncommitted progenitors (positive only for c-Kit), the cells transformed by MLL-AF10 tend to differentiate into myeloid lineage with expression of lineage markers (FIG. 2e, FIG. 8) (Okada et al., (2005) Cell121:167-78). This observation is consistent with the fact that leukemia patients with CALM-AF10 often develop hematologic malignancy of multi-lineages, an indication that the leukemic cells have originated from a very early stage of hematopoietic development (Kobayashi et al., (1997) Genes Chromosomes Cancer20:253-9). Up-regulation of different Hoxa genes might be linked to these phenotypical differences. For example, constitutive expression of Hoxa5 in human CD34[+] cells prevents differentiation toward erythrocytes and increases myelopoiesis (Crooks et al., (1999) Blood 94:519-28). Although there is currently no report that overexpression of Hoxa5 in hematopoitic stem cells can directly cause leukemic transformation, many cell lines without MLL-fusion have a higher incidence of overexpressing Hoxa5 than overexpressing Hoxa9 (Quentmeier et al., (2004) Leuk Lymphoma 45:567-74, indicating that upregulation of Hoxa5 may not be limited to leukemia mediated by CALM-AF10.

The foregoing is illustrative of the present invention, and is not to be construed as limiting thereof. The invention is defined by the following claims, with equivalents of the claims to be included therein.

That which is claimed is:

1. A method of identifying a candidate compound for the prevention and/or treatment of leukemia, the method comprising:
contacting a DOT1L polypeptide with a CALM-AF10 fusion protein in the presence of a test compound under conditions sufficient for binding of the DOT1L polypeptide to the CALM-AF10 fusion protein; and
detecting interaction between the DOT1L polypeptide and the CALM-AF10 fusion protein,
wherein a reduction in interaction between the DOT1L polypeptide and the CALM-AF10 fusion protein in the presence of the test compound as compared with the level of interaction in the absence of the test compound indicates that the test compound is a candidate compound for the treatment of leukemia.

2. The method of claim 1, wherein DOT1L polypeptide interaction with the CALM-AF10 fusion protein is evaluated by determining binding between the DOT1L polypeptide and CALM-AF10.

3. The method of claim 1, wherein DOT1L polypeptide interaction with the CALM-AF10 fusion protein is evaluated by determining nuclear localization of CALM-AF10.

4. The method of claim 1, wherein DOT1L polypeptide interaction with the CALM-AF10 fusion protein is evaluated by determining histone H3 lysine 79 (H3-K79) methylation of HoxA5.

5. The method of claim 4, wherein the H3-K79 methylation of the HoxA5 promoter is determined.

6. The method of claim 1, wherein DOT1L polypeptide interaction with the CALM-AF10 fusion protein is evaluated by determining HoxA5 promoter activity.

7. The method of claim 6, wherein the HoxA5 promoter is operably associated with a heterologous nucleic acid encoding a reporter molecule, and the reporter molecule is detected.

8. The method of claim 7, wherein the reporter molecule is a polypeptide.

9. The method of claim 8, wherein the polypeptide is an enzyme.

10. The method of claim 1, wherein the DOT1L polypeptide and/or CALM-AF10 fusion protein is expressed from a nucleic acid.

11. The method of claim 1, wherein the leukemia is T cell acute lymphoid leukemia (T-ALL) or acute myeloid leukemia subtype M0/1 (AML-M0/1).

12. The method of claim 1, wherein the DOT1L polypeptide is a mammalian DOT1L polypeptide and the CALM-AF10 fusion protein is a mammalian CALM-AF10 fusion protein.

13. The method of claim 12, wherein the DOT1L polypeptide is a human DOT1L polypeptide and the CALM-AF10 fusion protein is a human CALM-AF10 fusion protein.

* * * * *

UNITED STATES PATENT AND TRADEMARK OFFICE
CERTIFICATE OF CORRECTION

PATENT NO. : 8,524,467 B2  
APPLICATION NO. : 12/161482  
DATED : September 3, 2013  
INVENTOR(S) : Zhang et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,359 days.

Signed and Sealed this
Eleventh Day of February, 2014

Michelle K. Lee
*Deputy Director of the United States Patent and Trademark Office*

SEQUENCE LISTING

<160> NUMBER OF SEQ ID NOS: 6

<210> SEQ ID NO 1
<211> LENGTH: 10
<212> TYPE: PRT
<213> ORGANISM: Mus musculus

<400> SEQUENCE: 1

Leu Ala Asn Leu Val Gly Asn Leu Gly Ile
1               5                   10

<210> SEQ ID NO 2
<211> LENGTH: 10
<212> TYPE: PRT
<213> ORGANISM: Homo sapiens

<400> SEQUENCE: 2

Leu Ala Ser Leu Val Gly Asn Leu Gly Ile

```
<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3
atcaggagca cagagctgtg a                                              21

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tatacagcca gcctgtcatg                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
agtggctgct ttgctttctc                                                20

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa denotes any amino acid residue
<220> FEATURE:
<221> NAME/KEY: MISC_FEATURE
<222> LOCATION: (3)..(4)
<223> OTHER INFORMATION: Xaa denotes the presence or absence of an amino
      acid residue, wherein present Xaa denotes any amino acid residue
<220> FEATURE:
<221> NAME/KEY: MISC_FEATURE
<222> LOCATION: (6)..(7)
<223> OTHER INFORMATION: Xaa denotes any amino acid residue
<220> FEATURE:
<221> NAME/KEY: MISC_FEATURE
<222> LOCATION: (8)..(8)
<223> OTHER INFORMATION: Xaa denotes the presence or absence of an amino
      acid residue, wherein present Xaa denotes any amino acid residue
<220> FEATURE:
<221> NAME/KEY: MISC_FEATURE
<222> LOCATION: (10)..(10)
<223> OTHER INFORMATION: Xaa denotes any amino acid residue

<400> SEQUENCE: 6

Leu Xaa Xaa Xaa Leu Xaa Xaa Xaa Leu Xaa Leu
1               5                   10
```